(12) United States Patent
San et al.

(10) Patent No.: US 7,256,016 B2
(45) Date of Patent: Aug. 14, 2007

(54) RECYCLING SYSTEM FOR MANIPULATION OF INTRACELLULAR NADH AVAILABILITY

(75) Inventors: Ka-Yiu San, Houston, TX (US); Susana J. Berrios-Rivera, Pearland, TX (US); George N. Bennett, Houston, TX (US)

(73) Assignee: Rice University, Houston, TX (US)

( * ) Notice: Subject to any disclaimer, the term of this patent is extended or adjusted under 35 U.S.C. 154(b) by 432 days.

(21) Appl. No.: 10/286,326

(22) Filed: Nov. 1, 2002

(65) Prior Publication Data

US 2003/0175903 A1   Sep. 18, 2003

Related U.S. Application Data

(60) Provisional application No. 60/335,371, filed on Nov. 2, 2001.

(51) Int. Cl.
*C12P 21/06* (2006.01)
*C12P 33/02* (2006.01)
*C12N 1/10* (2006.01)
*C12N 5/02* (2006.01)

(52) U.S. Cl. .................... 435/69.1; 435/61; 435/252.1

(58) Field of Classification Search .................... None
See application file for complete search history.

(56) References Cited

U.S. PATENT DOCUMENTS

| | | | |
|---|---|---|---|
| 4,766,071 | A | 8/1988 | Simon et al. |
| 5,264,092 | A | 11/1993 | Skotheim et al. |
| 5,302,520 | A | 4/1994 | Goux |
| 5,393,615 | A | 2/1995 | Corey et al. |
| 5,520,786 | A | 5/1996 | Bloczynski et al. |
| 6,001,590 | A | 12/1999 | Komeda et al. |
| 6,242,234 | B1 * | 6/2001 | Kula et al. .................. 435/191 |
| 6,312,933 | B1 * | 11/2001 | Kimoto et al. .............. 435/190 |
| 6,337,204 | B1 | 1/2002 | Monot et al. |
| 6,455,284 | B1 | 9/2002 | Gokarn et al. |

OTHER PUBLICATIONS

Tishkov VI and Popov VO. 2004. Catalytic Mechanism and Application of Formate Dehydrogenase. Biochemistry Moscow. 69(11):1252-1267.*
Galkin A, KulakovaL, Yoshimura Y, Soda K, Esaki N. 1997. Synthesis of Optically Active Amino Acids from alpha Keto Acids with *E. coli* Cells Expressing Heterologous Genes. Applied and Environ. Microbiol. vol. 63. pp. 4651-4656.*
Sakai Y, Murdanoto AP, Konishi T, Iwamatsu A, Kato N. 1997. Regulation of the Formate Dehydrogenase Gene, in teh Methylotrophic Yeast *C. boidinii* and Growth Characteristics of an FDH1-disrupted Strain. J. Bacteriol. vol. 179(14). pp. 4480-4485.*
Allen SJ, Holbrook JJ, Isolation, sequence and overexpression of the gene encoding NAD-dependent formate dehydrogenase from the methylotrophic yeast *Candida methylica*. Gene. Aug. 30, 1995;162(1):99-104.*

Slusarczyk H, Felber S, Kula MR, Pohl M. Stabilization of NAD-dependent formate dehydrogenase from *Candida boidinii* by site-directed mutagenesis of cysteine residues.Eur J Biochem. Mar. 2000;267(5):1280-9.*
Chou, Chih-Hsiung, et al.; Effect of Modulated Glucose Uptake on High-Level Recombinant Protein Production in a Dense *Escherichia coli* Culture; Biotechnol. Prog., vol. 10, pp. 644-647, 1994.
Aristidou, Aristos A., et al.; Metabolic Engineering of *Escherichia coli* To Enhance Recombinant Protein Production through Acetate Reduction; Biotechnol. Prog., vol. 11, pp. 475-478, 1995.
Kragl, Udo, et al.; Enzyme Engineering Aspects of biocatalysts: Cofactor Regeneration as Example; Biotechnology and Bioengineering, vol. 52, pp. 309-319, 1996.
Hummel, Werner, et al.; Review: Dehydrogenases for the synthesis of chiral compounds; Eur. J. Biochem. vol. 184, pp. 1-13, 1989.
Sakai, Yasuyoshi, et al.; Regulation of the Formate Dehydrogenase Gene, *FDH1*, in the Methylotrophic Yeast *Candida boidinii* and Growth Characteristics of an *FDH1*-Disrupted Strain on Methanol, Methylamine, and Choline; Journal of Bacteriology, vol. 179 (14), pp. 4480-4485, Jul. 1997.
Liberies, Stephen D., et al.; Inducible gene expression and protein translocation using nontoxic ligands identified by a mammalian three-hybrid screen; Proc. Natl. Acad. Sci. USA, vol. 94, pp. 7825-7830, Jul. 1997.
Yang, Yea-Tyng, et al.; Metabolic Flux Analysis of *Escherichia coli* Deficient in the Acetate Production Pathway and Expressing the *Bacillus subtilis* Acetolactate Synthase; Metabolic Engineering, vol. 1, pp. 26-34, 1999.
Foster, John W., et al.; Regulation of NAD Metabolism in *Salmonella typhimurium*: Molecular Sequenc Analysis of the Bifunctional *nadR* Regulator and the *nadA-pnuC* Operon; Journal of Bacteriology, vol. 172 (8), pp. 4187-4196, Aug. 1990.
San, Ka-Yiu, et al.; Metabolic Engineering through Cofactor Manipulation and Its Effects on Metabolic Flux Redistribution in *Escherichia coli*; Metabolic Engineering, vol. 4, pp. 182-192, 2002.
Lopez, Felix, et al.; Cofactor Engineering: a Novel Approach to Metabolic Engineering in *Lactococcus lactis* by Controlled Expression of NADH Oxidase; Journal of Bacteriology, vol. 180 (15), pp. 3804-3808, Aug. 1998.
De Graef, Mark R., et al.; The Steady-State Internal Redox State (NADH/NAD) Reflects the External Redox State and Is Correlated with Catabolic Adaptation in *Escherichia coli*; Journal of Bacteriology, vol. 181 (8), pp. 2351-2357, Apr. 1999.
Alam, Kiswar Y., et al.; Anaerobic Fermentation Balance of *Escherichia coli* as Observed by In Vivo Nuclear Magnetic Resonance Spectroscopy; Journal of Bacteriology, vol. 171 (11), pp. 6213-6217, Nov. 1989.
Riondet, Christophe, et al.; Extracellular Oxireduction Potential Modifies Carbon and Electron Flow in *Escherichia coli*; Journal of Bacteriology, vol. 182 (3), pp. 620-626, Feb. 2000.

(Continued)

*Primary Examiner*—Joseph Woitach
*Assistant Examiner*—Laura McGillem
(74) *Attorney, Agent, or Firm*—Baker & McKenzie LLP; Tamsen V. Valoir; Michael D. Berger

(57) ABSTRACT

The present invention describes a novel recombinant NADH recycling system that is used as a process for producing reduced compounds. In a specific embodiment, the reduced compounds include ethanol, succinate, lactate, a vitamin, a pharmaceutical and a biodegraded organic molecule. The NADH recycling system effects metabolic flux of reductive pathways in aerobic and anaerobic environments.

8 Claims, 9 Drawing Sheets

OTHER PUBLICATIONS

Aristidou, Aristos A., et al.; Metabolic Flux Analysis of *Escherichia coli* Expressing the *Bacillus subtilis* Acetolactate Synthase in Batch and Continuous Cultures; Biotechnol. Bioeng., vol. 63, pp. 737-749, 1999.

Galkin, Andrey, et al.; Synthesis of Optically Active Amino Acids from a-Keto Acids with *Escherichia coli* Cells Expressing Heterologous Genes; Applied and Environmental Microbiology, vol. 63 (12), pp. 4651-4656, Dec. 1997.

Baldoma, L., et al.; Metabolism of L-Fucose and L-Rhamnose in *Escherichia coli*: Aerobic-Anaerobic Regulation of L-Lactaldehyde Dissimilation; Journal of Bacteriology, vol. 170 (1), pp. 416-421, Jan. 1988.

Tishkov, Vladimir I., et al.; Pilot Scale Production and Isolation of Recombinant $NAD^+$—and $NADP^+$-Specific Formate Dehydrogenases; Biotechnol Bioeng, vol. 64, pp. 187-193, 1999.

Park, D. H., et al.; Utilization of Electrically Reduced Neutral Red by *Actinobacillus succinogenes*: Physiological Function of Neutral Red in Membrane-Driven Fumarate Reduction and Energy Conservation; Journal of Bacteriology, vol. 181 (8), pp. 2403-2410, Apr. 1999.

Leonardo, Michaell R., et al.; Anaerobic Regulation of the *adhE* Gene, Encoding the fermentative Alcohol Dehydrogenase of *Escherichia coli*; Journal of Bacteriology, vol. 175 (3), pp. 870-878, Feb. 1993.

PCT International Search Report, Aug. 6, 2004.

Berrios-Rivera SJ, Bennett GN, San KY. Metabolic engineering of *Escherichia coli*: increase of NADH availability by overexpressing an NAD(+)-dependent formate dehydrogenase. Metab Eng. Jul. 2002;4(3):217-29.

Berrios-Rivera SJ, Bennett GN, San KY. The effect of increasing NADH availability on the redistribution of metabolic fluxes in *Escherichia coli* chemostat cultures. Metab Eng. Jul. 2002;4(3):230-7.

Berrios-River SJ, San KY, Bennett GN. The effect of carbon sources and lactate dehydrogenase deletion on 1,2-propanediol production in *Escherichia coli*. J Ind Microbiol Biotechnol. Jan. 2003;30(1):34-40. Epub Jan. 3, 2003.

Berrios-Rivera SJ, San KY, Bennett GN. The effect of NAPRTase overexpression on the total levels of NAD, the NADH/NAD+ ratio, and the distribution of metabolites in *Escherichia coli*. Metab Eng. Jul. 2002;4(3):238-47.

Berrios-Rivera SJ, Sanchez AM, Bennett GN, San KY. Effect of different levels of NADH availability on metabolite distribution in *Escherichia coli* fermentation in minimal and complex media. Appl Microbiol Biotechnol. Sep. 2004;65(4):426-32. Epub Apr. 7, 2004.

Boonstra, B et al., Cofactor regeneration by a soluble pyridine nucleotide transhydrogenase for biological production of hydromorphone, Appl Environ Microbiol. Dec. 2000;66(12):5161-6.

Leonida, Redox enzymes used in chiral syntheses coupled to coenzyme regeneration, Curr Med Chem. Mar. 2001;8(4):345-369.

Maicas, S et al., NAD(P)H regeneration is the key for heterolactic fermentation of hexoses in *Oenococcus oeni*, Microbiology, Jan. 2002;148(Pt 1):325-32.

Yang YT, Bennett GN, San KY. Effect of inactivation of nuo and ackA-pta on redistribution of metabolic fluxes in *Escherichia coli*. Biotechnol Bioeng. Nov. 5, 1999;65(3):291-7.

* cited by examiner

----- · original NAD independent pathway
(FDHF: formate dehydrogenase, NAD independent)

——— Newly added NAD+ dependent pathway
(FDH1: NAD⁺-dependent formate dehydrogenase)

·············· NAD⁺- dependent pathway active under aerobic
conditions (PDH: pyruvate dehydrogenase)

- ■ GJT001(pDHK29)
- □ GJT001(pSBF2)
- ▨ BS1(pSBF2)
- □ BS1(pDHK30)
- ■ GJT001(pDHK29) + 50mM Formate
- ▨ BS1(pSBF2) + 50mM Formate

- ■ GJT001(pDHK29)
- ▫ GJT001(pSBF2)
- ▨ BS1(pSBF2)
- ▨ BS1(pDHK30)
- ■ GJT001(pDHK29) + 50mM Formate
- ▨ BS1(pSBF2) + 50mM Formate

- - - - original NAD independent pathway
(FDHF: formate dehydrogenase, NAD independent)

⎯⎯⎯⎯ Newly added NAD+ dependent pathway
(FDH1: NAD+ dependent formate dehydrogenase
FDH1 encoded by *fdh1* from *Candida boidinii*)

RECYCLING SYSTEM FOR MANIPULATION OF INTRACELLULAR NADH AVAILABILITY

This application claims priority to U.S. Provisional Application Ser. No. 60/335,371, filed Nov. 2, 2001, which is incorporated by reference herein in its entirety.

GOVERNMENT INTEREST

The present invention was developed with funds from the United States Government. Therefore, the United States Government may have certain rights in the invention.

BACKGROUND OF THE INVENTION

1. Field of the Invention

The present invention relates to the fields of microbiology, molecular biology, cell biology and biochemistry. More specifically, the present invention relates to manipulating reductive metabolic processes in vivo using genetic and metabolic engineering, thereby allowing external control of intracellular nicotinamide adenine dinucleotide (NADH) availability. Further, the present invention relates to a method of producing increased reduced metabolites such as ethanol through aerobic or anaerobic growth of a living system comprised of a recombinant NADH recycling system.

2. Related Art

The metabolic pathways leading to the production of most industrially important compounds involve oxidation-reduction (redox) reactions. Biosynthetic transformations involving redox reactions offer a significant economic and environmental advantage for the production of fine chemicals over conventional chemical processes, in particular those redox reactions requiring stereospecificity. Furthermore, biodegradation of toxic chemicals often also involves redox reactions.

Nicotinamide adenine dinucleotide (NAD) functions as a cofactor in over 300 redox reactions and regulates various enzymes and genetic processes (Foster et al., 1990). The NADH/NAD+ cofactor pair plays a major role in microbial catabolism in which a carbon source, such as glucose, is oxidized using NAD+ producing reducing equivalents in the form of NADH. It is crucially important for continued cell growth that this reduced NADH be oxidized to NAD+ and a redox balance be achieved. Under aerobic growth, oxygen achieves this recycling by acting as the oxidizing agent. While under anaerobic growth, and in the absence of an alternate oxidizing agent, the regeneration of NAD+ is achieved through fermentation by using NADH to reduce metabolic intermediates.

The metabolic pathways leading to the production of most industrially important compounds involve redox reactions. Biosynthetic transformations involving redox reactions also offer a considerable potential for the production of fine chemicals over conventional chemical processes, especially those requiring stereospecificity.

Enzymes referred to in general as oxidoreductases, or more specifically as oxidases, reductases or dehydrogenases, catalyze these biological redox reactions. These enzymes require a donor and/or an acceptor of reducing equivalents in the form of electrons, hydrogen or oxygen atoms. Cofactor pairs that are transformed reversibly between their reduced and oxidized states, nucleotide cofactors such as NADH/NAD+ and NADPH/NADP+ among others, serve as donors and/or acceptors of reducing equivalents very effectively in a living cell.

The NADH/NAD+ cofactor pair has demonstrated a regulatory effect on gene expression and enzymatic activity. Examples include, among others, the induction by NADH of adhE expression, which encodes an alcohol dehydrogenase (Leonardo et al., 1993; Leonardo et al., 1996) and catalyzes the production of ethanol during fermentation, the inhibition by high NADH/NAD+ ratios on the pyruvate dehydrogenase complex (Graef et al., 1999), and the regulation by the NADH/NAD+ ratio on the shift between oxidation or reduction of L-lactaldehyde (Baldoma and Aguilar, 1988).

The ratio of the reduced to oxidized form of this cofactor, the NADH/NAD+ ratio, is critical for the cell. The NAD(H/+) cofactor pair is very important in microbial catabolism, where a carbon source, such as glucose, is oxidized through a series of reactions utilizing NAD+ as a cofactor and producing reducing equivalents in the form of NADH. It is crucially important for the continued growth of the cell that this reduced NADH be oxidized to NAD+, thus achieving a redox balance. Under aerobic growth, oxygen achieves this by acting as the oxidizing agent. While under anaerobic growth and in the absence of an alternate oxidizing agent, this process occurs through fermentation, where NADH is used to reduce metabolic intermediates and regenerate NAD+ (FIG. 1).

The high influence of cofactors in metabolic networks has been evidenced by studies in which the NADH/NAD+ ratio has been altered by feeding carbon sources possessing different oxidation states (Alam and Clark, 1989; Leonardo et al., 1996), by supplementing anaerobic growth with different electron acceptors, such as fumarate and nitrate (Graef et al., 1999) and by expressing an enzyme like NADH oxidase (Lopez de Felipe et al., 1998). Other previous efforts to manipulate NADH levels have included the addition of electron dye carriers (Park and Zeikus, 1999) and the variation of oxidoreduction potential conditions (Riondet et al., 2000).

The effective regeneration of used cofactors is critical in industrial cofactor-dependent production systems because of the impeding high cost of cofactors such as NAD. The cofactors, also referred to as co-enzymes, NAD+ and NADP+ are expensive chemicals, thereby making their regeneration by reoxidation to the original state imperative if they are to be used economically in low cost, chemical production systems. Efforts to do such have been described. U.S. Pat. No. 4,766,071 describes in vitro regeneration of NADH using a cell lysate of *Clostriduim kluyveri* as a biocatalyst and an aldehyde as an oxidizing agent. U.S. Pat. No. 5,393,615 describes electrochemical regeneration of NADH using an electrode characterized by a mediator function. Similarly, U.S. Pat. No. 5,264,092 discloses mediators covalently attached to a polymeric backbone wherein the polymeric backbone coats the surface of an electrode. U.S. Pat. No. 5,302,520 discloses a NAD regeneration system and an adenosine phosphate regeneration system that, in the presence of pyruvate, yields a labeled carbohydrate.

In enzyme bioreactors, NAD+-dependent formate dehydrogenase (FDH) from methylotrophic yeast and bacteria is extensively used to regenerate NADH from NAD+ in vitro. FDH catalyzes the practically irreversible oxidation of formate to $CO_2$ and the simultaneous reduction of NAD+ to NADH. This system of cofactor regeneration has been successfully applied in the production of optically active amino acids (Galkin et al., 1997), chiral hydroxy acids, esters, alcohols, and other fine chemicals synthesized by different dehydrogenases (Hummel and Kula, 1989), (Tishkov et al., 1999). Purified FDH has also been used to regenerate NADH in vitro for the industrial production of non-natural amino acids that cannot be obtained by fermentation, such as L-tert-leucine which has important applications when used in pharmaceuticals (Kragl et al., 1996).

In spite of these advances, biotransformation with whole cells remains the preferred industrial method for the synthesis of most cofactor-dependent products. In these systems, the cell naturally regenerates the cofactor; however, the enzyme of interest has to compete for the required cofactor with a large number of other enzymes within the cell. For this reason, in cofactor-dependent production systems utilizing whole cells, after the enzymes of interest have been overexpressed, cofactor levels and the availability of the required form of the cofactor (reduced or oxidized) become crucial for optimal production.

Furthermore, one of the long-sought goals in recombinant polypeptide production processes is to achieve a high cloned gene expression level and high cell density. Unfortunately, under these demanding conditions, the amount of acetate accumulated in the reactor increases precipitously. Acetate accumulation is associated with decreased recombinant polypeptide productivity (Aristidou et al, 1995). Methods of controlling acetate production would be beneficial in increasing recombinant polypeptide yield in large-scale industrial synthesis of polypeptides. Additionally, the sort of metabolic manipulation used to increase recombinant polypeptide yields could also be applied to the production of any biomolecule in a large-scale system in which the stress of biomolecule production normally leads to acetate accumulation, such as biopolymers.

Catalytic hydrodesulfurization has the potential to remove sulfur from various fuels. However, this technology is associated with high costs due to hydrogen consumption and heavy metal deactivation of the catalyst. A lower cost treatment is microbiological biodesulfurization. U.S. Pat. No. 6,337,204 describes a *Rhodococcus* bacterial culture capable of biodesulfurization. One obstacle in this method is that these reactions require NADH as a cofactor, the availability of which is a limiting factor.

Although it is generally known that cofactors play a major role in the production of different fermentation products, their role has not been studied thoroughly and systematically in engineered systems. Instead, metabolic engineering studies have focused on manipulating enzyme levels through the amplification, addition or deletion of a particular pathway. Such steps relegate cofactor manipulations as a powerful tool for metabolic engineering, as many enzymes require them. The dehydrogenases are but one example of selective catalysis requiring the energy-transferring redox couple, NADH/NAD+.

Prior to the present invention, a genetic means of manipulating the availability of intracellular NADH in vivo by regenerating NADH through the heterologous expression of an NAD+-dependent formate dehydrogenase was not known. By way of the present invention, the effect of manipulating intracellular NADH on the metabolic patterns in *Escherichia coli* under anaerobic and aerobic conditions by substituting the native cofactor-independent formate dehydrogenase (FDH) by an NAD+-dependent FDH such as from *Candida boidinii* is described. This manipulation provoked a significant change in the final metabolite concentration pattern both anaerobically and aerobically. Under anaerobic conditions, the production of more reduced metabolites was favored, as evidenced by a dramatic increase in the ethanol to acetate ratio. Unexpectedly during aerobic growth, the increased availability of NADH induced a shift to fermentation even in the presence of oxygen by stimulating pathways that are normally inactive under these conditions.

SUMMARY OF THE INVENTION

The present invention is directed to a method for increasing the intracellular availability of NADH, comprising the transformation of a cell with a nucleic acid encoding an NAD+-dependent dehydrogenase and growth of said cell under conditions in which said NAD+-dependent dehydrogenase increases the intracellular availability of NADH. In a specific embodiment, the NAD+-dependent dehydrogenase is a formate dehydrogenase. In a futher specific embodiment, the formate dehydrogenase is *Candida boidinii* formate dehydrogenase.

The present invention is directed to methods of utilizing a recombinant NADH recycling system to produce NADH and other metabolites in vivo. One embodiment of the present invention is a method to produce NADH in vivo comprising growing a culture of cells that comprises at least one cell, comprising a recombinant NADH recycling system. In a specific embodiment of the invention, the cell which comprises the recombinant NADH recycling system is a bacterium, including *E. coli*. In further specific embodiments of the invention, the recombinant NADH recycling system comprises a nucleotide sequence encoding a NAD+-dependent formate dehydrogenase, which may be from, but is not limited to, yeast, or *Candida boidinii*, operatively linked to a promoter In another embodiment of the present invention, there is a cell comprising a recombinant NADH recycling system. In specific embodiments, the recombinant NADH recycling system of the cell comprises a nucleotide sequence encoding a NAD+-dependent formate dehydrogenase operatively linked to a promoter. In a specific embodiment, the sequence is heterologous.

Yet another embodiment of the invention is a method to produce a reduced compound in vivo comprising growing a culture of cells that comprises at least one cell comprising a recombinant NADH recycling system. In a specific embodiment, the reduced compound produced is ethanol, lactate, succinate, a vitamin, a pharmaceutical or a biodegraded organic molecule. In a further specific embodiment, the pharmaceutical compound is an antibiotic. In another specific embodiment, the growing of cell culture takes place in an oxygen-deficient atmosphere. In another specific embodiment, the growing is in an oxygen-rich atmosphere. In another specific embodiment, formate is added to the culture of cells. In a further specific embodiment, the amount of formate added is at least about 100 mM.

In an additional embodiment of the present invention there is a method to produce ethanol comprising growing a culture of cells wherein the culture comprises at least one cell comprising a recombinant NADH recycling system.

Yet another embodiment of the invention is a method of altering metabolic flux of a reduction pathway comprising growing a culture of cells, wherein the culture comprises at least one cell comprising a recombinant NADH recycling system, and the flux of the metabolic pathway is redistributed as compared to a normal metabolic flux of the pathway.

Another embodiment of the invention is a method of biodegradation in vivo comprising growing a culture of cells, wherein the culture comprises at least one cell comprising a recombinant NADH recycling system.

Yet another embodiment of the present invention is a method for biodesulfurization in vivo comprising growing a culture of cells, wherein the culture comprises at least one cell comprising a recombinant NADH recycling system. In a further embodiment, the cells are bacteria cells. In a specific embodiment, the bacterial cells are *Rhodococcus* bacteria.

Another embodiment of the present invention is a method of biopolymer production in vivo comprising growing a culture of cells, wherein the culture comprises at least one cell comprising a recombinant NADH recycling system.

One embodiment of the present invention is a method for polypeptide production in vivo comprising growing a culture of cells, wherein the culture comprises at least one cell comprising a recombinant NADH recycling system. A specific embodiment is the production of heterologous recombinant protein.

Other embodiments, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF SUMMARY OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Definitions

Figure 1:
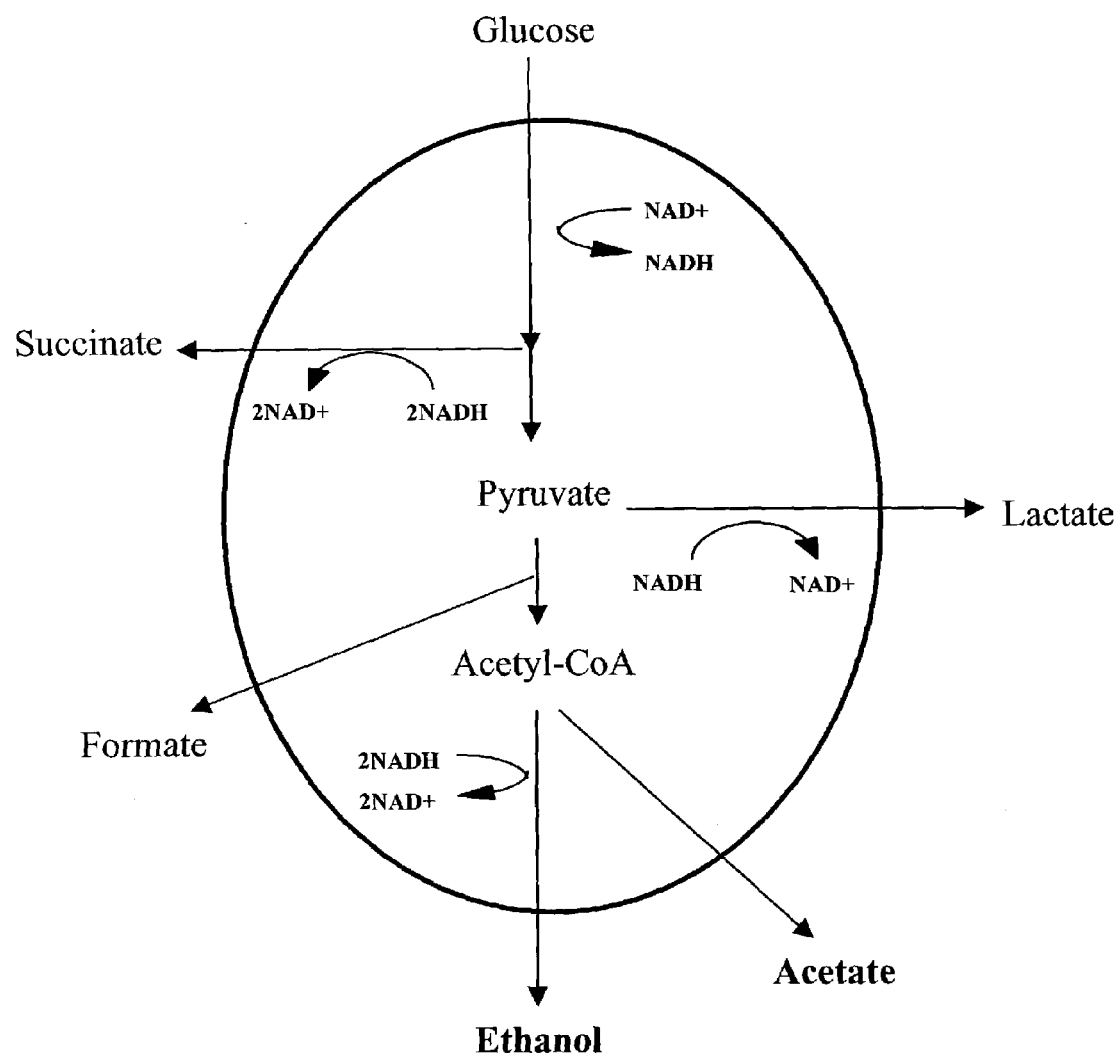
FIG. 1. Schematic representation of *Escherichia coli* central anaerobic metabolic pathways illustrating involvement of the NADH/NAD+ cofactor pair.

As used herein the specification, "a" or "an" may mean one or more. As used herein in the claim(s), when used in conjunction with the word "comprising", the words "a" or "an" may mean one or more than one. As used herein "another" may mean at least a second or more.

As used herein, the expressions "cell", "cell line" and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, the term "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid. Recombinant DNA refers to DNA which has been modified by joining genetic material from two different sources, which may be different species or the same species. Recombinant polypeptides may be the gene products of recombinant DNA, or polypeptides produced in recombinant cells. The term "recombinant NADH recycling system" refers to an engineered system for the recycling of NADH. It can refer to cells that comprise this system, or recombinant DNA or polypeptide sequences that comprise such a system.

The terms "modified" or "modification" as used herein refer to the state of a metabolic pathway being altered in which a step or process in the pathway is increased or upregulated, such as in activity of an enzyme or expression of a nucleic acid sequence, respectively. In a specific embodiment, the modification is the result of an alteration in a nucleic acid sequence which encodes an enzyme in the pathway, an alteration in expression of a nucleic acid sequence which encodes an enzyme in the pathway, or an alteration in translation or proteolysis of an enzyme in the pathway (i.e., formate dehydrogenase), or a combination thereof. A skilled artisan recognizes that there are commonly used standard methods in the art to obtain the alterations, such as by mutation.

Nucleic acid is "operatively linked" when it is placed into a functional relationship with another nucleic acid sequence. For example, DNA for a presequence or secretory leader is operatively linked to DNA for a polypeptide if it is expressed as a preprotein that participates in the secretion of the polypeptide; a promoter or enhancer is operatively linked to a coding sequence if it affects the transcription of the sequence; or a ribosome binding site is operatively linked to a coding sequence if it is positioned so as to facilitate translation. Generally, "operatively linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

"Plasmids" are designated by lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

One embodiment of the present invention is to provide a method to produce NADH in vivo comprising growing a culture of cells that comprises at least one cell comprising a recombinant NADH recycling system, under conditions to produce NADH. The NADH recycling system comprises a nucleic acid sequence encoding a dehydrogenase that is NAD+-dependent formate, such as FDH. The recombinant NADH recycling system increases the intracellular availability of NADH. FDH catalyzes the practically irreversible oxidation of formate to $CO_2$ and the simultaneous reduction of NAD+ to NADH. A skilled artisan is aware that NADH and NAD+ refer to nicotinamide adenine dinucleotide in two distinct oxidation states, respectively, and are cofactors that mediate a large number of biological oxidations and reductions, which generally provide a step or steps in catabolic metabolic pathways. When a substrate is hydrolyzed (in the instant case, formate is the substrate) hydride ($H^-$) is transferred to the C-4 of the nicotinamide ring of NAD+, and the $H^+$ is lost to the medium. Further, a skilled artisan recognizes that a dehydrogenase such as formate dehydrogenase catalyzes a reversible hydride transfer, generally a stereospecific reaction owing to the two distinct domains that the dehydrogenase protein conforms, in which each domain is specific for the binding of cofactor or substrate.

A skilled artisan recognizes that sequences useful in the present invention may be obtained in a database such as the National Center for Biotechnology's GenBank database. For example, a NAD+-dependent FDH1 of *Candida boidinii* (SEQ ID NO: 1, GenBank Accession NO: AF004096) and is a non-limiting example of a suitable FDH of the present invention. SEQ ID NO: 1 and any other nucleotide sequences encoding the polypeptide SEQ ID NO: 2 (GenBank Accession NO: AAC49766) are suitable. Other suitable FDHs are from *Candida methylica* (SEQ ID NO: 3, GenBank Accession NO: CAA57036), Pseodomonas sp. 101 (SEQ ID NO: 4, GenBank Accession NO: P33160), *Arabidopsis thaliana* (SEQ ID NO: 5, GenBank Accession NO: AAF19436), and *Staphylococcus aureus* (SEQ ID NO: 6, GenBank Accession NO: BAB94016). Any nucleic acids encoding SEQ ID NOS: 3, 4, 5, and 6 are also appropriate. Other species in embodiments of the invention are contemplated, such as *Saccharomyces bayanus, Saccharomyces exiguus, Saccharomyces servazzii, Zygosaccharomyces rouxii, Saccharomyces kluyveri, Kluyveromyces thermotolerans, Kluyveromyces lactis, Kluyveromyces marxianus, Pichia angusta, Debaryomyces hansenii, Pichia sorbitophila, Candida tropicalis* and *Yarrowia lipolytica*. Standard methods and reagents in the field of molecular biology are well known in the art. A reference for such methods includes *Current Protocols in Molecular Biology*, Chapter 13 (Ausubel et al., 1994), herein incorporated by reference.

In a preferred embodiment, the nucleic acid sequence encoding the non-native FDH is inserted into a vector such that the expression of the non-native FDH is controlled by a promoter that is operatively linked to the non-native FDH. A skilled artisan is aware of appropriate vectors and promoters, not excluding the native promoter of the non-native FDH gene, for expression of a recombinant gene in a host organism and methods to develop a resulting recombinant plasmid. The recombinant plasmid comprising the non-native FDH and promoter are then transformed into a host cell by methods well known in the art.

In a specific embodiment the host organism is an anaerobe, such as, for example, *Escherichia coli*, a facultative anaerobe that grows either in the presence or the absence of oxygen, or any aerotolerant organism that is capable of fermentation. In another specific embodiment, the wild-type FDH gene is inactivated, meaning that the nucleic acid sequence encoding for the native FDH gene is inoperative. For example, the fdhF (SEQ ID NO:7, GenBank Accession NO: M13563) of *E. coli* is replaced by homologous recombination using methods well known in the art. Engineering a host cell such that an enzymatic activity is removed can be screened, in one manner, by confirming the lack of the enzymatic activity in the recombinant host cell. Upon expression of the plasmid, the recombinant FDH gene assumes the responsibility of providing the respective enzymatic activity (e.g. dehydrogenation) for the host cell.

For example, the nucleic acid sequence of the formate dehydrogenase is regulated by an inducible promoter.

The recombinant cell is grown in an oxygen-rich atmosphere (aerobic) or in an oxygen-deficient atmosphere (anaerobic) to produce NADH, thereby increasing intracellular availability of NADH.

By increasing intracellular NADH availability, the present invention provides a method to produce a reduced metabolite comprising growing a culture of cells that comprises at least one cell comprising a recombinant NADH recycling system, and removing the reduced metabolite from the culture. The NADH recycling system effects increased intracellular NADH availability as compared to a control cell and consequently accumulates reduced products and metabolites such as, for example, reduced metabolites of glucose.

The method to produce reduced metabolites of the present invention includes metabolites not originally synthesized by the host cell. For example, in vivo reduction provided by the present invention is applied to biodegradation of toxic chemicals and/or semi-synthesis of a compound, wherein the compound is, for example, a vitamin or a pharmaceutical or a medicament. The pharmaceutical compound may be an antibiotic, such as tetracycline, amoxicillin, erythromycin, or zithromycin. Often the syntheses of such compounds to an appropriate oxidation state is required to, for example, ensure solubility, and such requirements include a reduction reaction. In such cases, the method of the present invention is contemplated especially involving a reduction reaction where stereospecificity is desired.

In yet another object of the present invention is a method to produce ethanol comprising growing a culture of cells that comprises at least one cell comprising a recombinant NADH recycling system, and removing the ethanol from the culture.

Another object is a method to produce lactate comprising growing a culture of cells, wherein the culture comprises at least one cell comprising a NADH recycling system, wherein the lactate may be removed from the culture.

It is another object of the present invention to provide a method to produce succinate comprising growing a culture of cells, wherein the culture comprises at least one cell comprising a NADH recycling system, wherein the succinate may be removed from the culture.

One object is a method of altering metabolic flux of a metabolic pathway comprising growing a culture of cells, wherein the culture comprises at least one cell comprising a NADH recycling system. The present invention enables the altering of metabolic flux of a reduction pathway to produce a reduced metabolite or reduced compound.

In a specific embodiment, the compound to be degraded is an environmental toxin, such as a toxic organic or inorganic compound. A skilled artisan recognizes that a toxic organic pollutant (also referred to as a xenobiotic) includes but is not limited to benzene, toluene, ethylbenzene, o-xylene, m-xylene, p-xylene, phenol, o-cresol, m-cresol, p-cresol, or styrene, as well as halogenated organic compounds such as pentachlorophenol. Examples of other environmental toxins include petroleum hydrocarbons (such as fuel oil or gasoline), insecticides (such as polychlorinated biphenyls (PCBs) or DDT), halogenated hydrocarbons, chlorinated benzenes, chlorophenols, chloroquaiacols, chloroveratroles, chlorocatechols, chlorinated aliphatics, perchlorates, nitrates, hydrolysates, or polycyclic aromatic hydrocarbons (PAHs, such as phenanthrene).

Another object of the present invention is a method of biodesulfurization in order to remove sulfur from fossil fuels, such as crude oil. Such an embodiment comprises at least one cell comprising an NADH recycling system where the NADH produced is a necessary cofactor for the enzymes involved in the biodesulfurization pathway. Dibenzothiophene is a model compound for organic sulfur in fossil fuels. Known members of the dibenzothiophene desulfurization pathway include dibenzothiophene monooxygenase, dibenzothipohene-5,5-dioxide monooxygenase, and 2'-hydroxybiphenly-2-sulfinate sulfinoylase. Known bacterial strains which are capable of breaking down dibenzothiophene using this pathway include *Rhodococcus* strains, including IGTS8, T09, and RA-18, and *Gordonia desulfuricans* 213E. Also capable of biodesulfurization are *E. coli* that express recombinant genes from *Rhodococcus*, and *Pseudomonas putida* that express recombinant genes from *Rhodococcus*. *Gordonia rubropertinctus* strain T08 is capable of biodesulfurization using a novel pathway. *Rhodococcus* strain IGTS8, *Gordonia rubropertinctus* strain T08, *E. coli*, and *Pseudomonas putida* are available from the American Type Culture Collection (ATCC). In one embodiment, a cell or cells comprising the NADH recycling system are transformed with vectors that are capable of expressing the gene products of the biodesulfurization pathway genes. In another embodiment, cells capable of biodesulfurization are transformed with a recombinant NADH recycling system. In such an embodiment, the cells capable of biodesulfurization may be *Rhodococcus* or recombinant *E. coli*.

It is an object of the present invention to create a method for the production of biopolymers in bacteria. Such an embodiment comprises at least one cell comprising an NADH recycling system where the NADH produced is a necessary cofactor for the enzymes involved in the biopolymer production pathway. The enzymes involved in the biopolymer production pathway may be host cell enzymes or recombinant enzymes. Biopolymers are polymers that are either naturally occurring or can be produced through engineering of a host organism. Examples of biopolymers are polysaccharides, polythioesters, polyhydroxybutyrates, polyhydroxyalkanoates. Other examples are chitins, starch, lignin, glycogen, cellulose, and xanthan gum. In some embodiments, biopolymers can also include polypeptides and amino acid polymers.

Another object of the present invention is a method of producing polypeptides in bacteria. The polypeptides produced may be under the transcriptional control of the host cell, or may be encoded by nucleic acids operatively linked to a promoter. The polypeptide may be of host cell origin or heterologous, and may be recombinant. Heterologous refers to polypeptides not naturally occurring in the host. Heterologous peptides may be from another species. Heterologous polypeptides may be encoded for by heterologous nucleic acids. Such an embodiment comprises at least one cell comprising an NADH recycling system where the NADH produced is able to shift the metabolic pattern of the cell to cause decreased acetate levels. Decreased acetate levels are associated with increased yields of recombinant polypeptide.

NUCLEIC ACID-BASED EXPRESSION SYSTEMS

1. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence. In specific embodiments, the promoter functions in a prokaryotic cell.

A promoter may be one naturally associated with a gene or sequence, as may be obtained by isolating the 5'-non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

b. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

c. Origins of Replication

In order to propagate a vector in a host cell, it may contain one or more origins of replication sites (often termed "ori"), which is a specific nucleic acid sequence at which replication is initiated. In specific embodiments, the origin of replication functions in a prokaryotic cell.

d. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Further examples of selectable and screenable markers are well known to one of skill in the art.

2. Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be prokaryotic, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials, which is readily accessible on the world wide web. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. Coli* LE392 could be used as host cells for phage viruses.

Similarly, a viral vector may be used in conjunction with a prokaryotic host cell, particularly one that is permissive for replication or expression of the vector.

Some vectors may employ control sequences that allow it to be replicated and/or expressed in prokaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Cells may be grown in culture medium. Culture medium may be liquid or solid. Liquid culture medium may be a broth. Solid medium may be molded into a plate. Liquid media are used for growth of pure batch cultures while solidified media are used widely for the isolation of pure cultures, for estimating viable bacterial populations, and a variety of other purposes. The usual gelling agent for solid or semisolid medium is agar, a hydrocolloid derived from red algae. Agar is used because of its unique physical properties (it melts at 100 degrees and remains liquid until cooled to 40 degrees, the temperature at which it gels) and because it cannot be metabolized by most bacteria. Hence as a medium component it is relatively inert; it simply holds (gels) nutrients that are in aqueous solution. Types of culture medium include differential, selective, minimal, and enrichment.

3. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

An expression system from STRATAGENE® (La Jolla, Calif.) is the pET E. COLI EXPRESSION SYSTEM is a widely used in vivo bacterial expression system due to the strong selectivity of the bacteriophage T7 RNA polymerase, the high level of activity of the polymerase and the high efficiency of translation. One of skill in the art would know how to express a vector, such as an expression construct, to produce a nucleic acid sequence or its cognate polypeptide, protein, or peptide.

4. Derivatives of Promoter Sequences

One aspect of the invention provides derivatives of specific promoters. One means for preparing derivatives of such promoters comprises introducing mutations into the promoter sequences. Such mutants may potentially have enhanced, reduced, or altered function relative to the native sequence or alternatively, may be silent with regard to function.

Mutagenesis may be carried out at random and the mutagenized sequences screened for function. Alternatively, particular sequences which provide the promoter region with desirable expression characteristics could be identified and these or similar sequences introduced into other related or non-related sequences via mutation. Similarly, non-essential elements may be deleted without significantly altering the function of the promoter. It is further contemplated that one could mutagenize these sequences in order to enhance their utility in expressing transgenes, especially in a gene therapy construct in humans.

The means for mutagenizing a DNA segment comprising a specific promoter sequence are well-known to those of skill in the art. Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, by introducing one or more nucleotide sequence changes into the DNA.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids also are routinely employed in site directed mutagenesis to eliminate the step of transferring the gene of interest from a plasmid to a phage.

Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al. (1995) provide two examples of such protocols.

The preparation of sequence variants of the selected promoter or intron-encoding DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, incorporated herein by reference. A number of template dependent processes are available to amplify the target sequences of interest present in a sample, such methods being well known in the art and specifically disclosed herein.

One efficient, targeted means for preparing mutagenized promoters or enhancers relies upon the identification of putative regulatory elements within the target sequence. These can be identified, for example, by comparison with known promoter sequences. Sequences which are shared among genes with similar functions or expression patterns are likely candidates for the binding of transcription factors and are likely elements to confer tissue specific expression patterns.

Other assays may be used to identify responsive elements in a promoter region or gene. Such assays will be known to those of skill in the art (see for example, Sambrook et al., 1989; Zhang et al, 1997; Shan et al., 1997; Dai and Burnstein, 1996; Cleutjens et al., 1997; Ng et al., 1994; Shida et al., 1993), and include DNase I footprinting studies, Electromobility Shift Assay patterns (EMSA), the binding pattern of purified transcription factors, effects of specific transcription factor antibodies in inhibiting the binding of a transcription factor to a putative responsive element, Western analysis, nuclear run-on assays, and DNA methylation interference analysis.

Preferred promoter constructs may be identified that retain the desired, or even enhanced, activity. The smallest segment required for activity may be identified through comparison of the selected deletion or mutation constructs. Once identified, such segments may be duplicated, mutated, or combined with other known or regulatory elements and assayed for activity or regulatory properties. Promoter region sequences used to identify regulatory elements can also be used to identify and isolate transcription factors that bind a putative regulatory sequence or element, according to standard methods of protein purification, such as affinity chromatography, as discussed above.

Preferably, identified promoter region sequences, whether used alone or combined with additional promoters, enhancers, or regulatory elements, will be induced and/or regulated by an external agent, such as a hormone, transcription factor, enzyme, or pharmaceutical agent, to express operatively linked genes or sequences (Zhang et al., 1997; Shan et al., 1997). Alternatively, such a construct may be designed to cease expression upon exposure to an external agent.

Following selection of a range of deletion mutants of varying size, the activities of the deleted promoters for expression of the linked CAT gene may be determined according to standard protocols.

The precise nature of the deleted portion of the promoter may be determined using standard DNA sequencing, such as Sanger dideoxy termination sequencing, to identify which promoter sequences have been removed in each of the assayed deletion mutants. Thus, a correlation may be obtained between the presence or absence of specific elements within the promoter sequence and changes in activity of the linked reporter gene.

5. FDH Nucleic Acids a. Nucleic Acids and Uses Thereof

Certain aspects of the present invention concern at least one FDH nucleic acid. In certain aspects, the at least one FDH nucleic acid comprises a wild-type or mutant FDH or nucleic acid. In particular aspects, the FDH or nucleic acid encodes for at least one transcribed nucleic acid. In certain aspects, the FDH or nucleic acid comprises at least one transcribed nucleic acid. In particular aspects, the FDH or nucleic acid encodes at least one FDH or protein, polypeptide or peptide, or biologically functional equivalent thereof. In other aspects, the FDH or nucleic acid comprises at least one nucleic acid segment of the exemplary SEQ ID NO:1, or at least one biologically functional equivalent thereof.

The present invention also concerns the isolation or creation of at least one recombinant construct or at least one recombinant host cell through the application of recombinant nucleic acid technology known to those of skill in the art or as described herein. The recombinant construct or host cell may comprise at least one FDH or nucleic acid, and may express at least one FDH or protein, peptide or peptide, or at least one biologically functional equivalent thereof.

As used herein "wild-type" refers to the naturally occurring sequence of a nucleic acid at a genetic locus in the genome of an organism, and sequences transcribed or translated from such a nucleic acid. Thus, the term "wild-type" also may refer to the amino acid sequence encoded by the nucleic acid. As a genetic locus may have more than one sequence or alleles in a population of individuals, the term "wild-type" encompasses all such naturally occurring alleles. As used herein the term "polymorphic" means that variation exists (i.e., two or more alleles exist) at a genetic locus in the individuals of a population. As used herein "mutant" refers to a change in the sequence of a nucleic acid or its encoded protein, polypeptide or peptide that is the result of the hand of man.

A nucleic acid may be made by any technique known to one of ordinary skill in the art. Non-limiting examples of synthetic nucleic acid, particularly a synthetic oligonucleotide, include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. Pat. No. 5,705,629, each incorporated herein by reference. A non-limiting example of enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells, such as recombinant DNA vector production in bacteria (see for example, Sambrook et al. 1989, incorporated herein by reference).

A nucleic acid may be purified on polyacrylamide gels, cesium chloride centrifugation gradients, or by any other means known to one of ordinary skill in the art (see for example, Sambrook et al. 1989, incorporated herein by reference).

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g. adenine "A," guanine "G," thymine "T" and cytosine "C") or RNA (e.g. A, G, uracil "U" and C). The term "nucleic acid" encompass the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss", a double stranded nucleic acid by the prefix "ds", and a triple stranded nucleic acid by the prefix "ts."

Thus, the present invention also encompasses at least one nucleic acid that is complementary to a FDH or nucleic acid. In particular embodiments the invention encompasses at least one nucleic acid or nucleic acid segment complementary to the sequence set forth in, for example, SEQ ID NO:1. Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" also refers to nucleic acid(s) that are substantially complementary, as may be assessed by the same nucleotide comparison set forth above. The term "substantially complementary" refers to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double stranded nucleic acid molecule during hybridization. In certain embodiments, the term "substantially complementary" refers to at least one nucleic acid that may hybridize to at least one nucleic acid strand or duplex in stringent conditions. In certain embodiments, a "partly complementary" nucleic acid comprises at least one sequence that may hybridize in low stringency conditions to at least one single or double stranded nucleic acid, or contains at least one sequence in which less than about 70% of the nucleobase sequence is capable of base-pairing with at least one single or double stranded nucleic acid molecule during hybridization.

6. Assays of Gene Expression

Assays may be employed within the scope of the instant invention for determination of the relative efficiency of gene expression. For example, assays may be used to determine the efficacy of deletion mutants of specific promoter regions in directing expression of operatively linked genes. Similarly, one could produce random or site-specific mutants of promoter regions and assay the efficacy of the mutants in the expression of an operatively linked gene. Alternatively, assays could be used to determine the function of a promoter region in enhancing gene expression when used in conjunction with various different regulatory elements, enhancers, and exogenous genes.

Gene expression may be determined by measuring the production of RNA, protein or both. The gene product (RNA or protein) may be isolated and/or detected by methods well known in the art. Following detection, one may compare the results seen in a given cell line or individual with a statistically significant reference group of non-transformed control cells. Alternatively, one may compare production of RNA or protein products in cell lines transformed with the same gene operatively linked to various mutants of a promoter sequence. In this way, it is possible to identify regulatory regions within a novel promoter sequence by their effect on the expression of an operatively linked gene.

In certain embodiments, it will be desirable to use genes whose expression is naturally linked to a given promoter or other regulatory element. For example, a prostate specific promoter may be operatively linked to a gene that is normally expressed in prostate tissues. Alteranatively, marker genes may be used for assaying promoter activity. Using, for example, a selectable marker gene, one could quantitatively determine the resistance conferred upon a tissue culture cell line or animal cell by a construct comprising the selectable marker gene operatively linked to the promoter to be assayed. Alternatively, various tissue culture cell line or animal parts could be exposed to a selective agent and the relative resistance provided in these parts quantified, thereby providing an estimate of the tissue specific expression of the promoter.

Screenable markers constitute another efficient means for quantifying the expression of a given gene. Potentially any screenable marker could be expressed and the marker gene product quantified, thereby providing an estimate of the efficiency with which the promoter directs expression of the gene. Quantification can readily be carried out using either visual means, or, for example, a photon counting device.

A preferred screenable marker gene for use with the current invention is β-glucuronidase (GUS). Detection of GUS activity can be performed histochemically using 5-bromo-4-chloro-3-indolyl glucuronide (X-gluc) as the substrate for the GUS enzyme, yielding a blue precipitate inside of cells containing GUS activity. This assay has been described in detail (Jefferson, 1987). The blue coloration can then be visually scored, and estimates of expression efficiency thereby provided. GUS activity also can be determined by immunoblot analysis or a fluorometric GUS specific activity assay (Jefferson, 1987). Similarly, 5-bromo-4chloro-3-indolyl galactoside (X-gal) is often used as a selectable marker, which confers a blue color on those transformants that comprise β-galactosidase activity.

EXAMPLES

The following examples are included to demonstrate preferred embodiments of the invention. It should be appreciated by those skilled in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Methods to Construct Bacterial Strain and Plasmid

Figure 2:
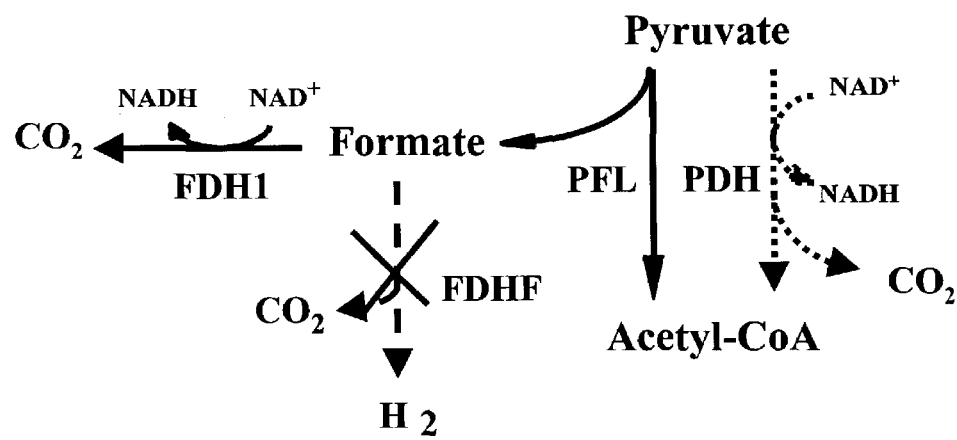
FIG. 2. Diagram illustrating the native cofactor-independent formate degradation pathway and the newly introduced NAD+-dependent pathway.

The strain BS1 was constructed from the strain GJT001 (Tolentino et al., 1992) by inactivating the native formate dehydrogenase. The exemplary plasmid pSBF2 contains the fdh1 gene from the yeast *Candida boidinii* (SEQ ID NO:1) under the control of the lac promoter. The fdh1 gene encodes an NAD+-dependent formate dehydrogenase (FDH) that converts formate to $CO_2$ with the regeneration of NADH from NAD+. This is in contrast with the native formate dehydrogenase that converts formate to $CO_2$ and $H_2$ with no cofactor involvement (FIG. 2). Also shown in FIG. 2 is the conversion of pyruvate to acetyl-CoA and formate by pyruvate formate lyase (PFL) under anaerobic conditions and to acetyl-CoA and $CO_2$ by pyruvate dehydrogenase (PDH) under aerobic conditions.

Recombinant bacterial strains and plasmids used in this study are listed in Table 3.

TABLE 3

Bacterial strains and plasmids

| | Significant genotype |
|---|---|
| Strains | |
| GJT001 | Spontaneous cadR mutant of MC4100, $Sm^R$ |
| DH10B | Cloning host |
| M9s | MC4100 φ(fdhF'-'lacZ), $Ap^R$ |
| BS1 | GJT001 φ(fdhF'-'lacZ), $Ap^R$ |
| Plasmids | |
| pUC18 | Cloning vector, $Ap^R$ |
| pDHK29, pDHK30 | Control, cloning vector, $Km^R$ |
| pFDH1 | fdh1 in pBluescriptII SK + |

TABLE 3-continued

Bacterial strains and plasmids

| | Significant genotype |
|---|---|
| PUCFDH | Intermediate plasmid, fdh1 in pUC18, $Ap^R$ |
| pSBF2 | fdh1 in pDHK30, $Km^R$ |

Strain BS1 was constructed by replacing the wild-type fdhF gene with a fdhF'-'lacZ fusion by a P1 vir-mediated phage transduction with E. coli M9s (Pecher et al., 1983) as donor and E. coli GJT001 as recipient. The P1 phage transduction was performed following standard protocols (Maniatis et al., 1989). Ampicillin resistant transductants were selected for further analysis. The lack of formate dehydrogenase activity was confirmed by a previously described method with minor modifications (Mandrand-Berthelot et al., 1978). Briefly, wild type and transduced GJT001 were grown on glucose minimal media plates for two days in an anaerobic chamber under an atmosphere of $H_2$ and $CO_2$. An overlay solution composed of 0.6% agar, 2 mg/ml benzyl viologen, 0.25M sodium formate and 25 mM $KH_2PO_4$ (pH 7.0) was poured over the plates. The presence of formate dehydrogenase activity in the wild type GJT001 was evidenced by a change in color of the colonies, which turned purple. The colonies of the transductants remained white, thus indicating the lack of formate dehydrogenase activity. The presence of the mutation of fdhF in the transductants was also confirmed by PCR. Primers complementary to the ends of the fdhF gene (forward primer SEQ ID NO:8, 5'-GATTAACTGGAGCGAGACC-3'; reverse primer SEQ ID NO:9, 5'-TCCGAAAGGAGGCTGTAG-3')(Zinoni et al., 1986) were used to amplify this gene in both wild type and transduced GJT001. The disruption of the fdhF gene in the transduced strain was confirmed by the absence of a PCR product as opposed to a 2.2-kb product corresponding to the complete gene in the wild type strain.

Plasmid pFDH1 was kindly provided by Dr. Y. Sakai (Sakai et al., 1997). It contains a 3 kb EcoRI insert containing the fdh1 gene from the yeast Candida boidinii in pBluescriptII SK+. The fdh1 gene in this plasmid is under the control of its native promoter. Preliminary experiments with this plasmid showed no FDH activity, suggesting that fdh1 from the yeast was not properly expressed in E. coli. For this reason, the open reading frame of the fdh gene from C. boidinii was amplified by PCR and placed under the control of the lac promoter for overexpression in E. coli.

XL-PCR was performed using the GeneAmp XL PCR kit from PE Applied Biosystems following the manufacturer's protocol. This kit was chosen because of the proofreading ability of the enzyme rTth DNA Polymerase, Polymerase, which not only promotes efficient DNA synthesis but also corrects nucleotide misincorporations. Plasmid pFDH1 was used as a template and the following were used as forward and reverse primers respectively: forward primer SEQ ID NO:10, 5'-GCGGAATTCAGGAGGAATTTAAAATGAA-GATCGTTTTAGTCTTATATGAT GCT-3'; reverse primer SEQ ID NO 11, 5'-CGCGGATCCTTATTTCTTATCGT-GTTTACCGTAAGC-3'. An EcoRI and a BamHI site were inserted in the forward and reverse primers respectively, as represented by the underlined regions.

The program used for the PCR reaction consisted of an initial denaturation step at 94° C. for 1 minute and 30 seconds followed by 18 cycles of denaturation at 94° C. for 30 seconds and combined annealing/extension at 55-66° C. for 5 minutes. This was followed by 12 cycles in which the annealing/extension time was increased by 15 seconds in each cycle until it reached 8 minutes. A final step at 72° C. for 10 minutes concluded the PCR.

The PCR product was verified by agarose gel electrophoresis. It was purified from the reaction mixture and concentrated following the protocol of the STRATAPREP™ PCR Purification Kit (STRATAGENE™-La Jolla, Calif.). The purified fdh PCR product and the vector pUC18 were digested with EcoRI and BamHI. Both fragments were ligated and the ligation product was transformed into E. coli strain DH10B. White colonies from Ap/Xgal/IPTG plates were selected for further analysis and minipreps were performed. Insertion of the fdh gene was confirmed by agarose gel electrophoresis after digestion with EcoRI/SalI.

This plasmid served as an intermediate vector to facilitate the insertion of the fdh gene into pDHK30 (Phillips et al., 2000) in the right orientation. It was ultimately desired to have the fdh gene in the pDHK30 backbone because it is a high copy number plasmid with kanamycin resistance, which will not interfere with the ampicillin resistance of the BS1 strain. An additional advantage of this vector is that it can be co-transformed in a two-plasmid system together with the most common high copy number vectors bearing a ColE1 origin.

The intermediate plasmid containing fdh (pUCFDH), and pDHK30 were digested with EcoRI/XbaI and ligated to obtain plasmid pSBF2. The ligation product was transformed into DH10B and white colonies from Km/Xgal plates were analyzed. Minipreps were obtained and analyzed by agarose gel electrophoresis after digestion with EcoRI/XbaI. An appropriate plasmid was selected and transformed both into GJT001 and the fdh⁻ strain BS1. Strain GJT001 was also transformed with pDHK29, and BS1 was transformed with pDHK30 to serve as negative controls.

Example 2

FDH Activity Assay

Determining FDH activity of strains GJT001 (pSBF2) and BS1 (pSBF2) comprised growing a culture of cells overnight in LB media supplemented with 20 g/L glucose and 100 mg/L kanamycin (Km) under anaerobic conditions. The cultures were inoculated with 100 µl of a 5 ml overnight LB culture and grown in a shaker at 37° C. and 250 rpm. Cells were harvested by centrifugation of 20 ml of culture at 4,000 g and 4° C. for 10 minutes. The pellet was suspended in 10 ml of 10-mM sodium phosphate buffer (refrigerated) at pH 7.5 with 0.1M β-mercaptoethanol and centrifuged as described above. The cells were resuspended in 10 ml of 10-mM sodium phosphate buffer (refrigerated) at pH 7.5 with 0.1M β-mercaptoethanol and sonicated for 6 minutes in an ice bath (Sonicator: Heat System Ultrasonics, Inc. Model W-255; Settings: 60% cycle, max power=8). The sonicated cells were centrifuged at 1,500 g and 4° C. for 60 min to remove cell debris and reduce the NAD background. The formate dehydrogenase activity was assayed at 30° C. by adding 100 µl of cell extract to 1 ml of a reaction mixture containing 1.67 mM NAD+, 167 mM sodium formate and 100 mM β-mercaptoethanol in phosphate buffer pH 7.5 and measuring the increase in absorbance of NADH at 340 nm (Schutte et al., 1976) modified). One unit was defined as the amount of enzyme that produced 1 µmol of NADH per minute at 30° C. Total protein concentration in cell extracts was measured by Lowry's method (Sigma Kit) using bovine serum albumin as standard.

Example 3

Growth Experiments: Anaerobic and Aerobic Conditions

Growth experiments were conducted on strains GJT001 (pDHK29) and BS1 (pSBF2) by growing aerobically triplicate cultures in a rotary shaker at 37° C. and 250 rpm. The cultures were grown in 250-ml shake flasks containing 50 ml of LB media supplemented with 10 g/L glucose, 100 mg/L kanamycin, and 0 or 100 mM formate. The O.D. at 600 nm was measured every 30 minutes during the exponential growth phase.

The anaerobic tube experiments were performed using 40-ml or 45-ml glass vials with open top caps and PTFE/silicone rubber septa. Each vial was filled with 35 ml (40-ml vials) or 40 ml (45-ml vials) of LB media supplemented with 20 g/L glucose, 100 mg/L kanamycin, 0 or 50 mM formate, and 1 g/L $NaHCO_3$ to reduce the initial lag time that occurs under anaerobic conditions. The triplicate cultures were inoculated with 100 μl of a 5 ml LB overnight culture. After inoculation, air (6 ml) was removed with a syringe from the headspace to ensure anaerobic conditions. The cultures were grown in a rotary shaker at 37° C. and 250 rpm. A sample of the initial media was saved for analysis and samples were withdrawn with a syringe at 24 hour intervals (24, 48, and 72 hrs).

The aerobic experiment was performed by growing triplicate cultures aerobically using either 125-ml shake flasks containing 25 ml of LB media or 250-ml shake flasks containing 50 ml of LB media. The LB media was supplemented with about 10 g/L glucose, 100 mg/L kanamycin, and different amounts of formate. The cultures were inoculated with 50 μl or 100 μl of a 5 ml LB overnight culture and grown in a rotary shaker at 37° C. and 250 rpm. A sample of the initial media was saved for HPLC analysis and samples were collected after 24 hours of growth.

Example 4

Methods of Analysis

Cell density (OD) was measured at 600 nm in a Spectronic 1001 spectrophotometer (Bausch & Lomb, Rochester, N.Y.). Fermentation samples were centrifuged for 5 minutes in a microcentrifuge. The supernatant was filtered through a 0.45-micron syringe filter and stored chilled for HPLC analysis. The fermentation products and glucose concentrations were quantified using an HPLC system (Thermo Separation Products, Allschwil, Switzerland) equipped with a cation-exchange column (HPX-87H, BioRad Labs, Hercules, Calif.) and a differential refractive index detector. A mobile phase of 2.5 mM $H_2SO_4$ solution at a 0.6 ml/min flow rate was used, and the column was operated at 55° C.

Example 5

FDH Activity

The effect of increasing intracellular NADH availability by genetic engineering on the metabolic patterns of *Escherichia coli* under anaerobic and aerobic conditions was determined. More specifically, the effect of regenerating NADH by substituting the native cofactor-independent formate dehydrogenase in *E. coli* by the NAD+-dependent FDH from *Candida boidinii*, as well as the effect of supplementing the culture media with formate was demonstrated herein.

Plasmid pSBF2, containing the fdh1 gene from *Candida boidinii* under the control of the lac promoter, was constructed and characterized by determining the activity of the new FDH. Table 4 shows the specific FDH activity of strains BS1 (pSBF2) and GJT001 (pSBF2) in Units/mg of total protein. One unit is defined as the amount of enzyme that produced 1 μmol of NADH per minute at 30° C. Values shown are average of triplicates from anaerobic tube cultures. N.D.: not detected (less than 0.001 U/mg). The FDH activity of strain GJT001 (pSBF2) was 46% higher (0.416 U/mg) than the activity of BS1 (pSBF2) (0.284 U/mg). Control strains GJT001(pDHK29) and BS1(pDHK30) showed no detectable FDH activity.

TABLE 4

Specific FDH activity

| Strain | Activity (U/mg) |
|---|---|
| BS1 (pSBF2) | 0.284 ± 0.002 |
| GJT001 (pSBF2) | 0.416 ± 0.004 |
| GJT001 (pDHK29) | N.D. |
| BS1 (pDHK30) | N.D. |

The effect of substituting the native FDH with the NAD+-dependent pathway was characterized by calculating the specific growth rate (μ) of strains BS1 (pSBF2) and GJT001 (pDHK29) in aerobic shake flask experiments. Table 5 presents the results of these experiments with and without 100 mM formate. The specific growth rate of strain BS1 (pSBF2) was 35% lower (0.986±0.002) than that of GJT001 (pDHK29) (1.511±0.016) without formate supplementation. However, by the end of the fermentation the cell density of BS1 (pSBF2) was comparable to or even higher than that of GJT001 (pDHK29).

In addition, the effect on the specific growth rate of formate supplementation at the level of 100 mM was examined. Formate addition to the media lengthened the duration of the lag phase for both strains, but more for BS1 (pSBF2). The difference in the specific growth rate between BS1 (pSBF2) and GJT001 (pDHK29) decreases with addition of formate. Under these conditions, the specific growth rate of GJT001 (pDHK29) is only 10% higher. Addition of formate did not affect significantly the specific growth rate of BS1 (pSBF2), however; it decreased that of GJT100 (pDHK29) by 28%. As in the case without formate supplementation, the final cell density of BS1 (pSBF2) was comparable to that of GJT001 (pDHK29).

TABLE 5

Specific aerobic growth rate (μ) of strains BS1 (pSBF2) and GJT001 (pDHK29).

| Strains: | 0 mM Formate | 100 mM Formate |
|---|---|---|
| BS1 (pSBF2) | 0.986 ± 0.002 | 0.972 ± 0.014 |
| GJT001 (pDHK29) | 1.511 ± 0.016 | 1.086 ± 0.043 |

Values shown are average of triplicates.

Example 6

Increased Intracellular NADH Availability and Alcohol Production During Anaerobiosis Anaerobic tube experiments were performed with strains GJT001 (pDHK29), GJT001 (pSBF2), BS1 (pSBF2), and BS1 (pDHK30) to investigate the effect on the metabolic patterns of the elimination of the native FDH and the addition or substitution of the new FDH. FIGS. 3A to 3F illustrate the results of these experiments, including the final cell density (FIG. 3A), the amount of glucose consumed in millimolar (mM) (FIG. 3B), and the concentrations of different metabolites produced (mM) after 72 hours of culture (FIGS. 3C to 3F). Values shown are the average of triplicate cultures.

Figure 3A:
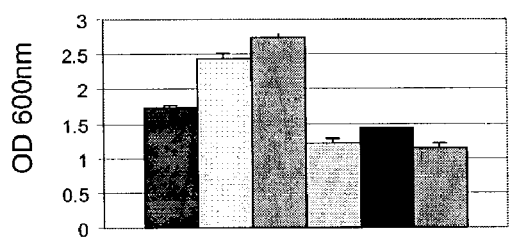
FIGS. 3A to 3F. Graphical illustrations of results of anaerobic tube experiments of strains after 72 hours.
Figure 3B:
Figure 3C:
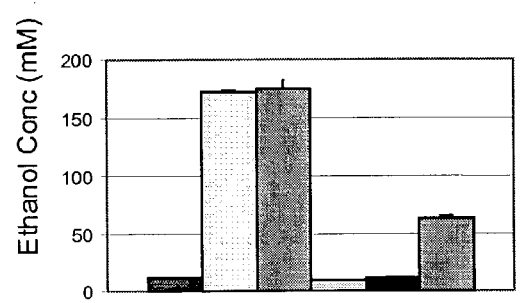
Figure 3D:
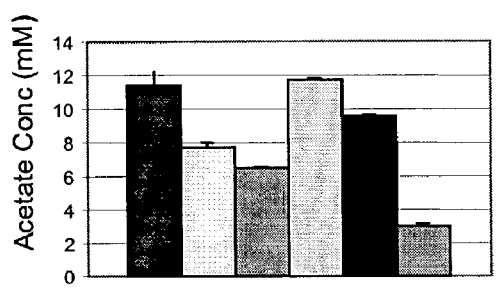
Figure 3E:
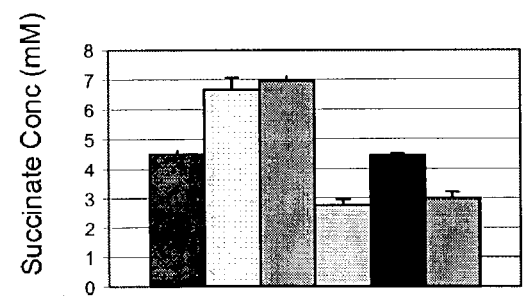
Figure 3F:
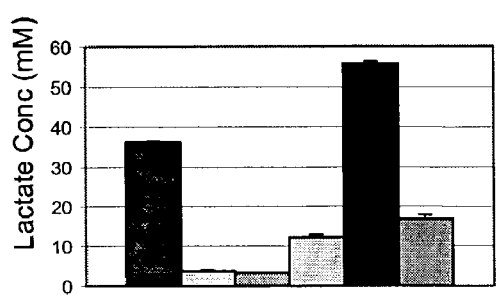

A comparison of the results for the control strains GJT001 (pDHK29) and BS1 (pDHK30) shows the effect of eliminating the native FDH on the metabolic patterns of E. coli. An increase in residual formate was observed for the strain lacking FDH activity. As shown in FIG. 3B, glucose consumption for BS1 (pDHK30) decreased by 47% relative to GJT001 (pDHK29). This led to a decrease in final cell density (29%; FIG. 3A), as well as, in succinate (39%; FIG. 3E), lactate (66%; FIG. 3F), and ethanol (22%; FIG. 3C) production. However, the level of acetate (FIG. 3D) was very similar to that of GJT001 (pDHK29). This translates into a decrease (24%) in the ethanol to acetate (Et/Ac) ratio. This decrease in the Et/Ac ratio together with the decrease in other reduced metabolites (lactate and succinate) indicates the presence of a more oxidized environment for the strain lacking formate dehydrogenase activity. These results suggest that under normal conditions GJT100 (pDHK29) recaptures a portion of the $H_2$ produced from the degradation of formate by the native FDH possibly by means of some hydrogenase, and this recapture accounts for the slightly more reduced intracellular environment observed for this strain relative to BS1 (pDHK30).

Table 6 gives the quantitative amounts of NADH in terms of $(NADH)_U/Gl$=moles of NADH available for reduced product formation per mole of glucose consumed, where $(NADH)_U$=Total NADH used for product formation per unit volume at the end of fermentation (mmol/L) and was estimated from the concentrations of reduced metabolites by calculating the NADH used for their production according to the pathways shown on FIG. 1., with 50 mM initial formate supplementation. Values shown are from average of triplicate cultures.

TABLE 6

NADH availability of various strains under anaerobic conditions.

| Strain | $(NADH)_u/Gl$ (mol/mol) |
|---|---|
| GJT001 (pDHK29) | 2.40 |
| GJT001 (pSBF2) | 4.34 |
| BS1 (pSBF2) | 4.35 |
| BS1 (pDHK30) | 2.38 |
| GJT001 (pDHK29) + F | 2.33 |
| BS1 (pSBF2) + F | 4.39 |

An analysis of the results for BS1 (pSBF2) relative to BS1 (pDHK30) and for GJT001 (pSBF2) relative to GJT001 (pDHK29) provides an understanding of the effect of overexpressing the NAD+-dependent FDH both alone or in conjunction with the native FDH, respectively. In both cases the trend is similar, but the effect is more pronounced for the BS1 strains due to the decrease in the metabolites observed for BS1 (pDHK30) relative to GJT001 (pDHK29). Both strains containing the new FDH present a significant increase in glucose consumption, cell density, ethanol, and succinate formation, accompanied by a decrease in lactate and acetate relative to the control strains. This translates into a dramatic increase in the ethanol to acetate (Et/Ac) ratio of 22-fold for GJT001 (pSBF2) and 35 to 36-fold for BS1 (pSBF2).

The results for GJT001 (pSBF2) and BS1 (pSBF2) show the effect of having both the native and new FDH active in the same strain or just the new FDH, respectively. A comparison of these results shows that these strains behave very similarly. The largest difference between these two strains is a 16% decrease in acetate, and consequently a 21% increase in Et/Ac ratio for BS1 (pSBF2) relative to GJT001 (pSBF2). This means that the NAD+-dependent FDH is competing effectively with the native FDH for available formate. This finding is supported by the fact that the Km value for formate of the native FDH is twice (26 mM) that of the NAD+-dependent FDH (13 mM) according to the literature (Schutte et al., 1976; Axley and Grahame, 1991). Although these results suggest that the fdh⁻ mutation is not necessary to observe the effect of overexpressing the NAD+-dependent FDH, the decrease in acetate levels observed for the fdh⁻ strain suggests that this mutation is be slightly beneficial in some cases.

Figure 4A:
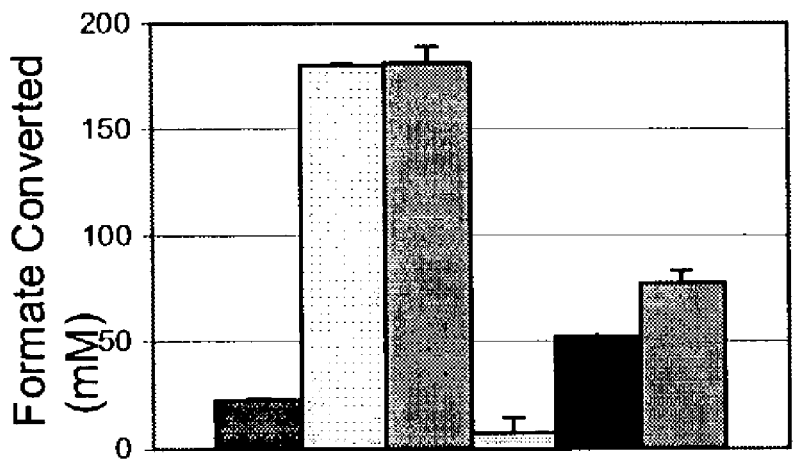
FIGS. 4A and 4B. Graphical illustrations of (A) formate consumed and ethanol/acetate ratio (B) of strains grown in anaerobic tube experiments.
Figure 4B:
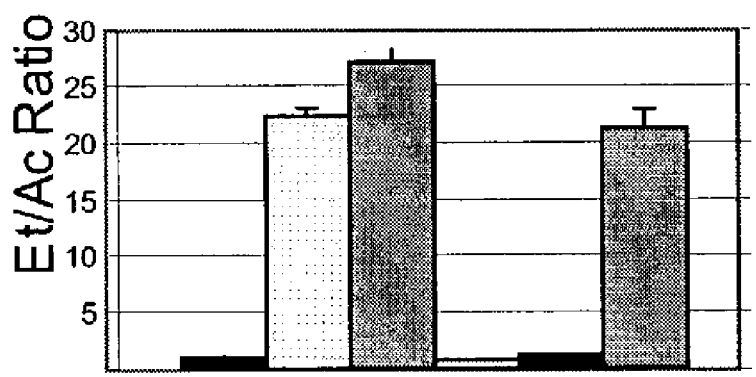
Figure 5A:
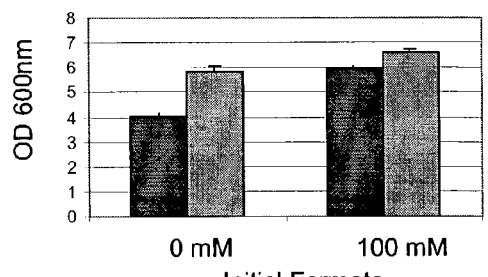
FIGS. 5A to 5F. Graphical illustrations of aerobic shake flask experiment after 24 hours.
Figure 5B:
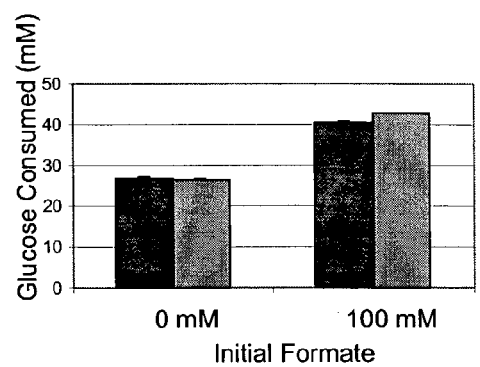
Figure 5C:
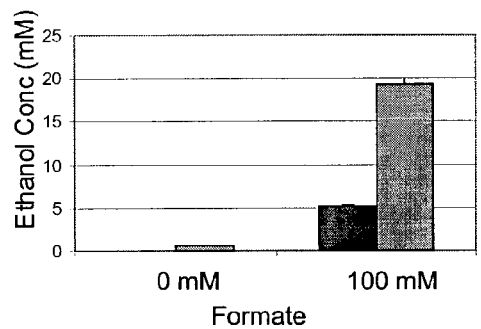
Figure 5D:
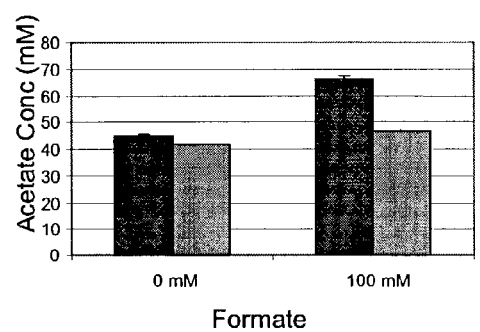
Figure 5E:
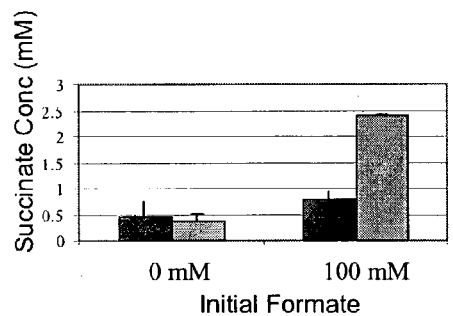
Figure 5F:
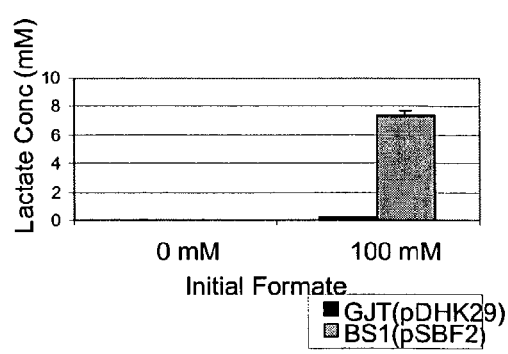

Analyzing the results of BS1 (pSBF2) relative to GJT001 (pDHK29) can better elucidate the effect of substituting the cofactor-independent native formate-degradation pathway in E. coli by the NAD+-dependent pathway. Substitution of the native FDH by the new FDH increased glucose consumption (3-fold), final cell density (59%), as well as the production of ethanol (15-fold) and succinate (55%), while it decreased lactate (91%) and acetate (43%) production (see FIGS. 3C to 3F). This translates into a dramatic increase in the ethanol to acetate (Et/Ac) ratio of 27-fold (FIG. 4B).

These results suggest that overexpression of the NAD+-dependent FDH increases intracellular NADH availability, and this in turn leads to a drastic shift in the metabolic patterns of E. coli. An increase in NADH availability favored the production of more reduced metabolites, particularly, those requiring 2NADH molecules per molecule of product formed, like ethanol and succinate. The preferred product was ethanol, with a final concentration reaching as high as 175 mM for BS1 (pSBF2), as compared to 11.5 mM for the wild type control, GJT001 (pDHK29). This makes ethanol the major fermentation product for BS1 (pSBF2) anaerobic cultures, accounting for 91% of the metabolites produced based on mM concentrations, as opposed to 18% for GJT001 (pDHK29). Simultaneously, lactate was converted from a major product, representing 57% of the produced metabolites in the wild type strain to only a minor product, accounting for less than 2% of the metabolites. This shift towards the production of ethanol as a major product is comparable to that obtained with overexpression of the ethanologenic enzymes from Zymomonas mobilis in the pet operon in E. coli (Ingram and Conway, 1988). Remarkably, these results indicate a significant production of ethanol despite the lack of overexpression of enzymes specifically directed towards ethanol production.

The dramatic increase in ethanol production combined with a decrease in acetate levels led to the drastic increase in the Et/Ac ratio observed, which reached as high as 27 for BS1 (pSBF2), as compared to 1.0 for GJT001 (pDHK-29). It is evident from these results that the cell adjusts its partitioning at the acetyl-CoA node by changing the ethanol (consumes 2 NADH) to acetate (consumes no NADH) ratio to achieve a redox balance, as was previously observed in experiments utilizing carbon sources with different oxidation states (San et al., 2001). These findings also support the idea that NADH induces expression of alcohol dehydrogenase (adhE) (Leonardo et al., 1996).

The significant decrease in lactate levels obtained with overexpression of the NAD+-dependent FDH can be explained by noting that although lactate formation also requires NADH, it only consumes 1 NADH, while ethanol formation consumes 2 NADH. These results suggest that when there is an excess of reducing equivalents, ethanol formation (2 NADH) is preferred over lactate formation (1 NADH) since it provides a faster route to NAD+ regeneration. These observations support previous findings in experiments utilizing carbon sources with different oxidation states (San et al., 2001).

FIGS. 3A to 3F and FIGS. 4A and 4B illustrate the results of anaerobic tube experiments performed with strains GJT001 (pDHK29) and BS1 (pSBF2) in which the media was supplemented with 50 mM formate. Addition of formate to both strains increased lactate levels. A comparison of the results for BS1 (pSBF2) and GJT001 (pDHK29) indicates a 6-fold increase in ethanol accompanied by a 69% decrease in acetate levels. This leads to a 21-fold increase in the Et/Ac ratio with the substitution of the native FDH for the NAD+-dependent FDH. This means that anaerobically it is not necessary to supplement the culture with formate.

The amounts of formate converted to $CO_2$ for the different strains, with and without formate addition under anaerobic conditions, were calculated by subtracting the measured residual formate concentration from the concentration of formate produced plus the initial formate concentration in the media for the experiments with formate supplementation. The amount of formate produced was obtained based on the assumption that one mol of formate is produced per mol of acetyl-CoA formed through the PFL pathway (see FIG. 2). Therefore, the amount of formate produced was calculated by adding the concentrations of ethanol and acetate formed from acetyl-CoA.

The data indicate that overexpression of the NAD+-dependent FDH drastically increases the conversion of formate almost equally for both strains BS1 (pSBF2) and GJT001 (pSBF2) suggesting that this new enzyme competes very effectively with the native FDH for the available formate. These two strains as well as GJT001 (pDHK29) converted all the formate produced during fermentation when there was no external formate added to the media, while strain BS1 (pDHK30) converted only minimal amounts of formate as expected.

It is also interesting to note that external addition of formate to the media had opposite effects on the native and new FDH. Formate supplementation of GJT001 (pDHK29) cultures significantly increased (2 to 3-fold) the amount of formate converted by the native enzyme, although only 78% of the available formate was converted. These results suggest that addition of extra formate has a stimulatory effect on this pathway or that initially the pathway was limited by the amount of formate, while after formate supplementation it became limited by the enzyme activity instead. In contrast, addition of formate to BS1 (pSBF2) anaerobic cultures decreased the amount of formate converted, with only 69% of the available formate being degraded, suggesting possible inhibition of the new FDH at these levels of formate. Plausibly, this decrease in formate conversion is the indirect consequence of a lower glucose consumption and optical density. Although the total levels of formate produced for this strain without external formate addition were higher than with the 50 mM supplementation, the cells did not experience high levels of formate at a given time because it is being degraded as it is produced. In contrast, in the supplementation experiment, the cell experienced a higher initial formate concentration.

Example 7

Increased Intracellular NADH Availability During Aerobiosis

Shake flask experiments were performed with strains GJT001 (pDHK29) and BS1 (pSBF2) to investigate the effect of increasing intracellular NADH availability by substituting the native FDH in *E. Coli* by the NAD+-dependent enzyme on the metabolic patterns under aerobic conditions. These experiments were performed with and without 100 mM formate supplementation. Addition of formate as a substrate for the new FDH during aerobic growth was necessary because under these conditions the cells normally do not produce formate due to lack of activity of the pyruvate formate lyase (PFL) enzyme. FIGS. 5A to 5F presents the results of these experiments, including the final cell density (FIG. 5A), glucose consumed (mM) (FIG. 5B), and the concentrations of different metabolites produced (mM) after 24 hours of culture (FIGS. 5C to 5F). For both strains only minimal amounts of residual formate (less than 6 mM) were detected.

Figure 6A:
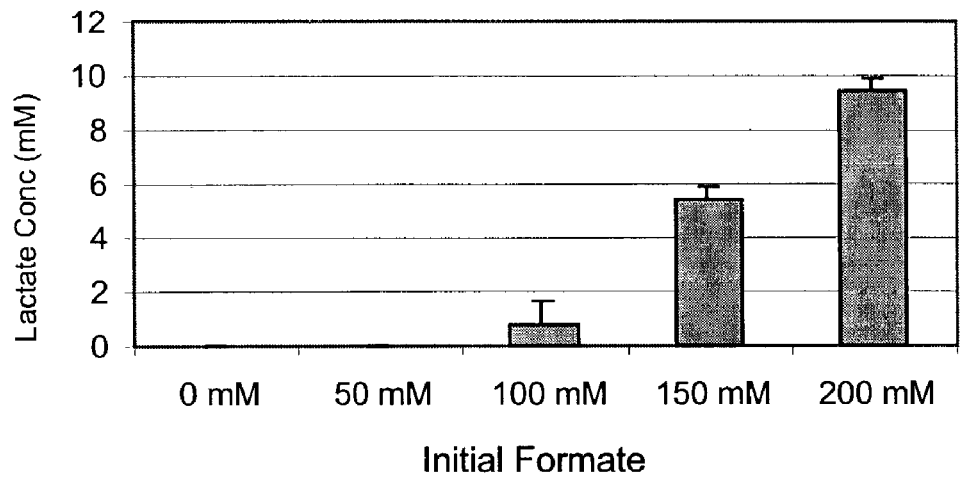
FIGS. 6A and 6B. Graphical illustrations of (A) lactate and (B) succinate concentrations from aerobic growth in various concentrations of supplemented formate.

This data indicate that addition of formate to BS1 (pSBF2) aerobic cultures induced the production of ethanol, lactate, and succinate, metabolites that are normally produced only under anaerobic conditions. The amount detected corresponds to a 36-fold increase in ethanol (FIG. 5C), 7-fold increase in succinate (FIG. 5E), and the production of lactate (FIG. 6A). Glucose consumption increased by 50% and acetate levels by 11%. The Et/Ac ratio increased by 32-fold.

Also addressed by this data is the effect of formate supplementation on the native FDH was also investigated. Addition of formate to GJT001 (pDHK29) aerobic cultures caused an increase of 50% in glucose consumption, the same percentage of increase observed for BS1 (pSBF2). However, the increase in acetate levels was much higher (47%) with formate supplementation, as well as the increase in final cell density (48%). On the other hand, the production of ethanol was much lower, only 5.15 mM after 24 hours, and succinate levels increased only by 72% compared to a 7-fold increase for BS1 (pSBF2).

The results obtained for both strains with formate supplementation shows a 27-fold increase in lactate, 4-fold increase in ethanol, 3-fold increase in succinate, accompanied by a 30% decrease in acetate (5-fold increase in Et/Ac) for the NAD+-dependent FDH relative to the native FDH. The glucose consumption was similar for both strains, while the final cell density was slightly higher for BS1 (pSBF2).

These results demonstrate that it is possible to increase the availability of intracellular NADH through the substitution of the native FDH in *E. Coli* by an NAD+-dependent FDH. The higher intracellular NADH levels provide a more reduced environment even under aerobic conditions. As a result, the cells utilize this extra NADH to reduce metabolic intermediates leading to the formation of fermentation products in order to achieve a redox balance. Conversely, under normal aerobic conditions, the environment is so oxidized that reduced fermentation products are not formed. Under aerobic conditions, only acetate, a more oxidized metabolite that does not require NADH, is normally produced. The results described herein also suggest that although the native FDH is able to indirectly recapture some of the extra reducing power in the formate added, the new FDH is a lot more effective because it recaptures this extra reducing power directly as NADH.

Example 8

Effect of Formate on Reduction Processes During Aerobiosis

Figure 6B:
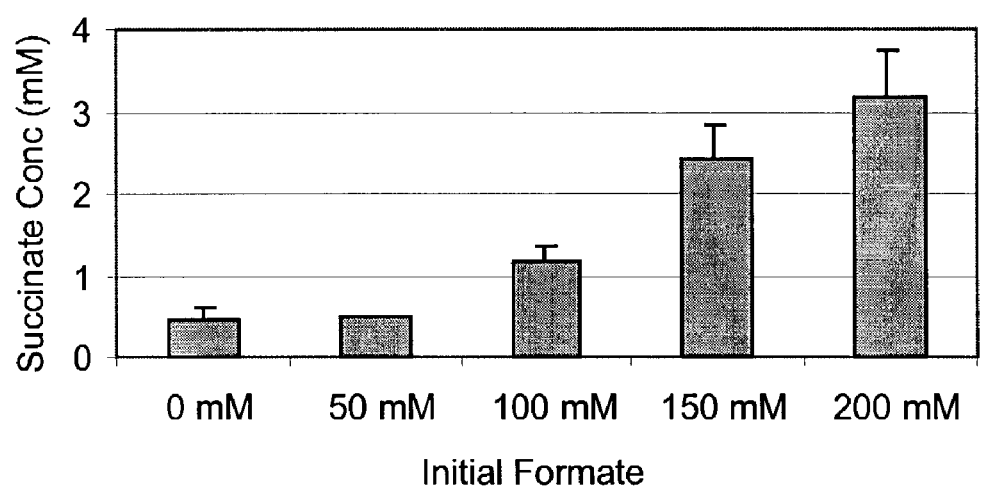
Figure 7:
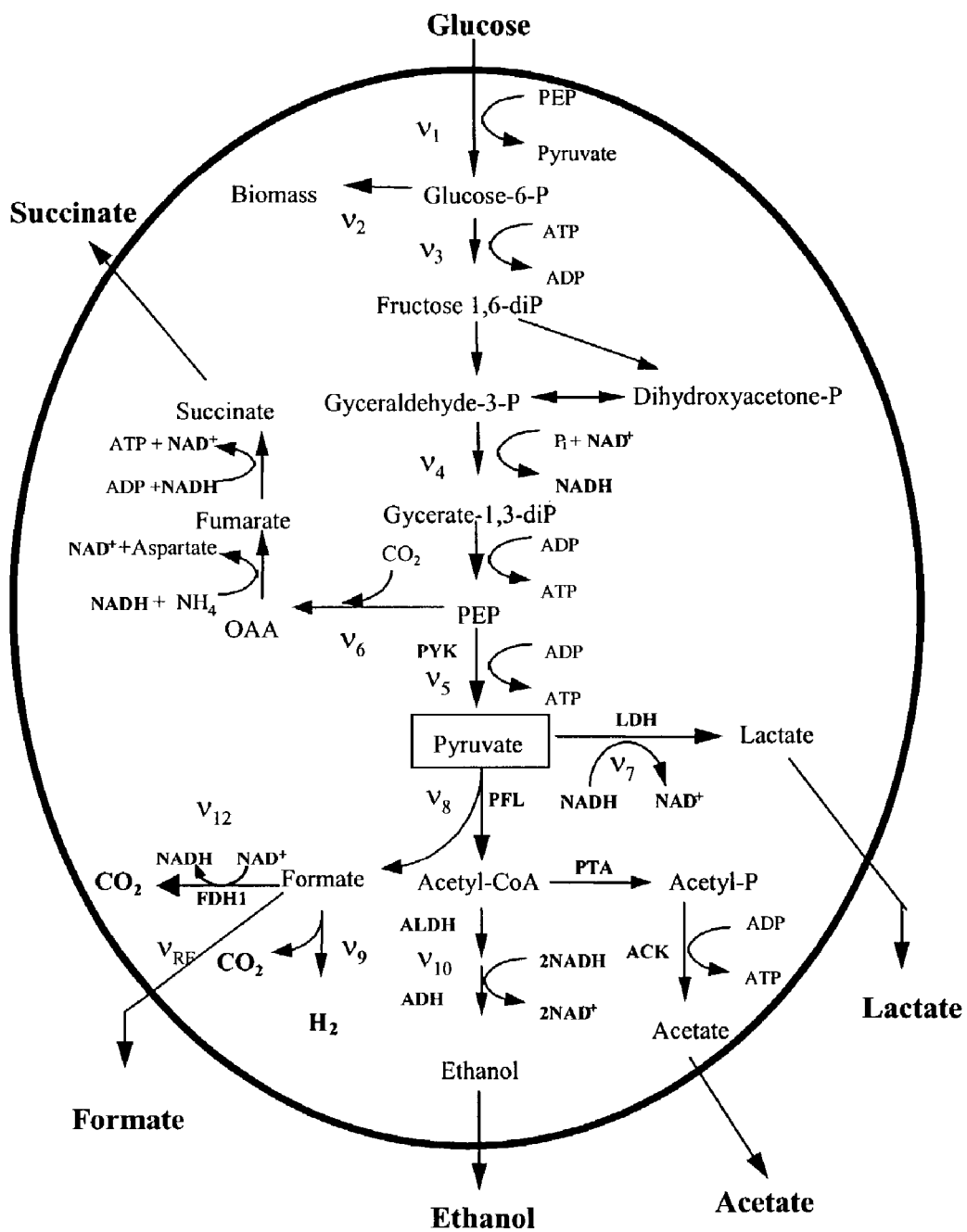
FIG. 7. Central aerobic metabolic pathway of *Escherichia coli* showing generation of NADH and regeneration of NAD+ and metabolic flux of each contributing pathway.

In addition, the effect of supplementing the media with different levels of formate (0, 50, 100, 150, and 200 mM) was investigated in aerobic cultures of BS1 (pSBF2). It is interesting to note that lactate was absent at 0 and 50 mM initial formate, but it was produced at 100, 150, and 200 mM initial formate (FIGS. 6A and 6B). The concentration of lactate increased with an increase in the initial formate levels. The same trend was evident in succinate production with the difference that similar levels were produced at 0 and 50 mM initial formate (FIG. 6B). On the other hand, the cells produced ethanol only after formate supplementation, but the levels did not significantly increase with an increase in formate levels. Acetate production and final cell density did not follow any notable trend with increasing levels of formate supplementation. Glucose consumption increased with addition of formate and remained constant with different formate levels because all the glucose was consumed by 24 hours in all the formate supplemented cultures.

It was also observed that the concentration of residual formate reached 63.5 mM for the 200 mM initial formate experiment, a 10-fold increase from the residual levels in the 150 mM experiment. The levels of residual formate were lower than 12 mM for all other initial formate levels. These findings possibly indicate that the culture is past saturation at this formate level. In addition, based on the formate conversion levels observed, more NADH is being generated by this pathway than that used to produce reduced metabolites. The cells are possibly using this extra NADH formed for ATP generation through the electron transport system since they are growing aerobically.

The results of the formate supplementation experiment show that different formate levels can be used to provide different levels of reducing power. Higher levels of reducing power aerobically mainly increased lactate production. In contrast, in anaerobic cultures with no formate supplementation, where the environment was a lot more reduced, ethanol production was highly increased, while lactate levels decreased. However, formate supplementation in anaerobic cultures provoked an increase in lactate levels, which is consistent with the aerobic case.

Example 9

Increasing Reductive Capabilities in vivo

The data indicates that it is possible to increase the availability of intracellular NADH through metabolic engineering, thereby providing enhanced reducing power under both anaerobic and aerobic conditions.

The substitution of the native cofactor independent FDH pathway by the NAD+-dependent FDH provoked a significant metabolic redistribution both anaerobically and aerobically. Under anaerobic conditions, the increased NADH availability favored the production of more reduced metabolites, as evidenced by a dramatic increase in the ethanol to acetate ratio for BS1 (pSBF2) as compared to the GJT1 (pDHK29) control (FIG. 4B). This led to a shift towards the production of ethanol as the major fermentation product (FIG. 3C).

Further during aerobic growth, the increased availability of NADH induced a shift to fermentation even in the presence of oxygen by stimulating pathways that are normally inactive under these conditions. Because formate is not a normal product under aerobic conditions, it was added to the media to increase NADH availability. The addition of formate to BS1 (pSBF2) aerobic cultures induced the production of ethanol, lactate, and succinate, metabolites that are normally produced only under anaerobic conditions.

Example 10

Chemostat Cultures

The novel approach to increasing availability of intracellular NADH in vivo through a NADH recycling system is applied to the production of commercially viable compounds, such as ethanol. The NADH recycling system comprises a biologically active NAD+-dependent formate dehydrogenase (FDH) from *Candida boidinii*, and overexpression thereof in *Escherichia coli*. The NADH recycling system (e.g., recombinant formate dehydrogenase pathway) produces one mole of NADH per one mole of formate converted to carbon dioxide (FIG. 2). This recombinant system bears contrast with the native formate dehydrogenase which converts formate to $CO_2$ and $H_2$ with no cofactor involvement. The new NADH recycling system allows the cells to retain the reducing power that are otherwise lost by release of formate or hydrogen.

The functionality of this approach was further characterized by evaluating anaerobic chemostat cultures in a controlled bioreactor environment.

Example 11

Methods of Anaerobic Chemostat Experiments

Initially, the inoculum was grown as a 5-ml LB culture supplemented with 100 mg/L ampicillin and/or kanamycin for 8-12 hours. Then, 100 µl of the 5-ml culture was transferred to 50 ml of LB in a 250-ml shake flask with the appropriate antibiotic, and grown at 37° C. and 250 rpm for 8-12 hours in a rotary shaker. This culture was used to inoculate the bioreactor.

Luria-Bertani broth (LB) medium supplemented with 110 mM of glucose, was used for the chemostat runs. To reduce the initial lag time that occurs under anaerobic conditions, 1 g/L $NaHCO_3$ was added to the LB media. The media was also supplemented with 30 µL/L antifoam 289 (Sigma), 100 mg/L ampicillin, and/or kanamycin.

The fermentations were carried under anaerobic chemostat conditions at a dilution rate of 0.2 $hr^{-1}$. A 2.5 L bioreactor (New Brunswick Scientific, Bioflo III) was used. It initially contained 1.3 L of medium during the anaerobic batch stage and then was maintained at 1.20 L working volume for the anaerobic chemostat stage. The pH, temperature and agitation were maintained at 7.0, 32° C., and 250 rpm, respectively. A constant flow of nitrogen (10-12 ml/min) was maintained through the fermentor headspace to establish anaerobic conditions. The continuous culture reached steady state after 4 to 6 residence times. Samples were taken during the steady state phase.

Cell dry weight was determined by collection of 100 ml of culture in an ice bath. The samples were centrifuged at 4,000 g and 4° C. for 10 minutes, washed with 0.15 M sodium chloride solution, and dried in an oven at 55° C. until constant weight. The final weight of the dried samples was corrected for the weight of NaCl in the washing solution.

For chromatography, samples of the fermentation broth were collected and centrifuged at 6000 g and 4° C. for 10 minutes in a Sorvall centrifuge (SS-34 rotor).

Example 12

FDH Activity in Anaerobic Chemostat Cultures

Experiments were performed under anaerobic chemostat conditions with strains GJT001 and BS1 containing a control plasmid to investigate the effect of eliminating the native formate dehydrogenase activity. The results of those experiments indicated that with inactivation of the native FDH, which converts formate to $CO_2$ and $H_2$, reducing power is lost in the form of formate. This resulted in a more oxidized intracellular environment as reflected by a significant decrease in the NADH/NAD+ ratio (48%) and a decrease in the Et/Ac ratio (19%). These observations are consistent with previously reported results under anaerobic tube conditions with these two strains. These results imply that under normal conditions when the native FDH is active, the cells are able to recapture some of the reducing power in the hydrogen released from the degradation of formate possibly by means of a native hydrogenase. These findings suggest that substitution of the native FDH by an NAD+-dependent FDH, which transfers the reducing equivalents directly from formate to NADH, provides a more reduced intracellular environment by recapturing more effectively the reducing power that otherwise is lost.

Anaerobic chemostat experiments were performed with strains GJT001 (pSBF2), BS1 (pSBF2), and GJT001 (pDHK29). Strain GJT001 (pDHK29) contains the native formate dehydrogenase (FDH) only, while strain BS1 (pSBF2) has the *C. boidinii* FDH, and GJT001 (pSBF2) has both FDH enzymes active. A chemostat mode was chosen because it allows the determination of the concentration of NADH and NAD+ and the metabolic fluxes during steady state. It also allows fixing of the specific growth rate for each strain by fixing the dilution rate (0.2 $h^{-1}$).

Table 7 presents the specific NAD+-dependent FDH activity of strains GJT001 (pSBF2) and BS1 (pSBF2) obtained from the anaerobic chemostat runs in units/mg of total protein. One unit is defined as the amount of enzyme that produced 1 μmol of NADH per minute at 30° C. As this table shows, the specific FDH activity of both strains was very similar. Strain GJT001(pDHK29) showed no detectable FDH activity. One unit is defined as the amount of enzyme that produced 1 μmol of NADH per minute at 30° C. Values shown are average of triplicates. N.D.: not detected (less than 0.001 U/mg).

TABLE 7

Specific NAD+-dependent FDH activity.

| Strain | Activity (U/mgTP) |
|---|---|
| GJT001 (pSBF2) | 0.242 ± 0.009 |
| BS1 (pSBF2) | 0.231 ± 0.007 |
| GJT001 (pDHK29) | N.D. |

Example 13

Metabolic Flux Redistribution in Anaerobic Chemostat Cultures

Steady state concentrations of metabolites are given in Table 8 as millimolar (mM) units as measured by the HPLC, as well as the percent of $CO_2$ and $H_2$ per volume in the off-gases stream as measured by the GC. The concentrations are in anaerobic chemostat (average of three samples) at D=0.2 $h^{-1}$. $CO_2$ and $H_2$ in % per volume as measured from the off-gases by GC. Dry weight (D.W.) in g/L.

Figure 8:
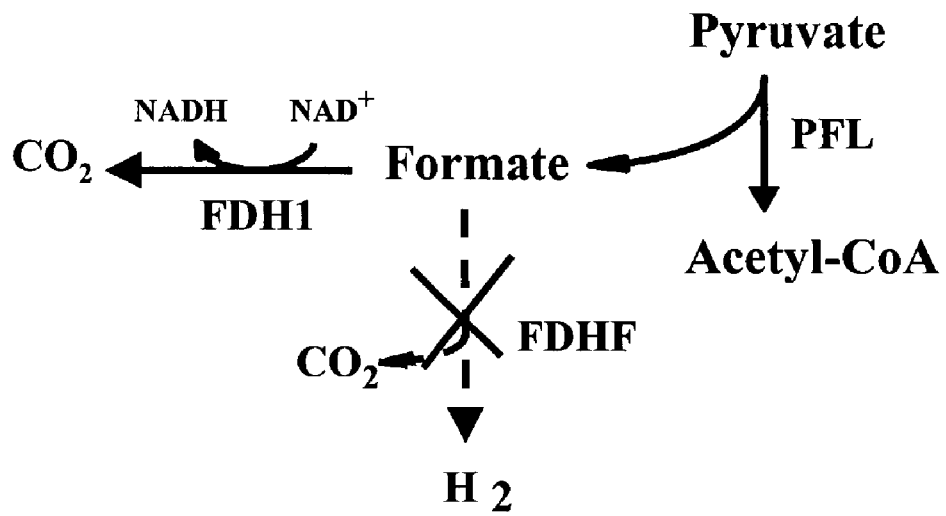
FIG. 8. Diagram illustrating the native cofactor-independent formate degradation pathway and the recombinant NADH recycling system.

Table 9 presents the results as calculated metabolic fluxes in mmol/(g dry weight*h) represented as $v_1$ to $v_{12}$ according to the diagram illustrated in FIG. 8. Note that $v_{12}$ represents the newly added NAD+-dependent FDH pathway. In addition, $v_{RF}$ represents the flux of residual formate excreted to the media based on HPLC measurements. The metabolic fluxes with an asterisk were calculated based on measured metabolites, while the other fluxes were derived from the measured metabolites based on the relationships shown in FIG. 8, the law of mass conservation, and the pseudo-steady-state hypothesis (PSSH) on the intracellular intermediate metabolites as described previously (Aristidou et al., 1999; Yang et al, 1999). Metabolic fluxes with an asterisk were calculated based on measured metabolites, while the other fluxes were derived from the measured metabolites based on the relationships shown in FIG. 8. The percentages of increase (+) or decrease (−) presented are relative to strain GJT001 (pDHK29). The "+" indicates that the culture comprised the newly added NAD+-dependent FDH pathway.

Table 10 includes the NAD(H/+) concentrations in μmol/g dry weight (D.W.) in addition to the NADH formed through the oxidation of glucose and the new FDH degradation pathway, as well as the NADH utilized for the formation of reduced metabolites, namely, succinate, lactate, and ethanol. The percentages of increase (+) or decrease (−) presented on these tables are relative to strain GJT001 (pDHK29), and are an average of three samples at a dilution, D=0.2 $h^{-1}$. $(R_{NADH})_f$=specific NADH formation rate=$v_4+v_{12}$; $(R_{NADH})_u$=specific NADH utilization rate=$2v_6+v_7+2v_{10}$. Both rates are in units of mmol/(gD.W.*h). The percentages of increase (+) or decrease (−) are determined relative to strain GJT001 (pDHK29).

The overexpression of the NAD+-dependent FDH drastically changed the distribution of metabolic fluxes in *E. coli*. The most notable effect observed is the shift in the ethanol to acetate ratio (Et/Ac), which indicates an increase in intracellular NADH availability. This ratio increased from 1.06 for the control strain to 3.47 for the strain with the new FDH and 3.82 for the strain with both enzymes coexpressed. This represents a 3 to 4-fold increase in the Et/Ac ratio relative to the control. These findings are similar to the results obtained when sorbitol (Et/Ac=3.62), a more reduced carbon source that can therefore produce more reducing equivalents in the form of NADH, was used instead of glucose (Et/Ac=1.00) in anaerobic chemostat experiments (San et al., 2001).

TABLE 8

Metabolite concentrations of recombinant strains.

| Strain | GJT001 (pDHK29) | GJT001 (pSBF2) | BS1 (pSBF2) |
|---|---|---|---|
| Glucose Consumed | 113.36 ± 0.59 | 94.74 ± 3.99 | 64.43 ± 4.98 |
| Succinate | 13.50 ± 0.31 | 9.49 ± 1.33 | 5.05 ± 0.46 |
| Lactate | 37.37 ± 0.60 | 4.38 ± 0.41 | 1.96 ± 0.32 |
| Residual Formate | 64.35 ± 0.96 | 36.89 ± 3.66 | 43.91 ± 2.04 |
| Acetate | 74.26 ± 0.77 | 35.75 ± 2.74 | 25.88 ± 1.09 |
| Ethanol | 78.86 ± 0.97 | 136.54 ± 8.78 | 89.70 ± 6.62 |
| Et/Ac | 1.06 | 3.82 | 3.46 |
| $CO_2$ | 11.58 ± 0.38 | 16.25 ± 2.89 | 10.71 ± 0.93 |
| $H_2$ | 16.95 ± 0.05 | 7.01 ± 0.59 | 0.02 ± 0.02 |
| D.W. | 2.48 ± 0.03 | 1.31 ± 0.01 | 2.03 ± 0.08 |

TABLE 9

Anaerobic chemostat results.

| Flux | To: | GJT001 (pDHK29) | GJT001 (pSBF2) | % Inc/Dec | BS1 (pSBF2) | % Inc/Dec |
|---|---|---|---|---|---|---|
| $v_1$ | Glucose Uptake* | 7.81 | 12.93 | 65.63 | 5.53 | −29.20 |
| $v_2$ | Biosynthesis | 0.78 | 0.23 | −71.06 | 0.27 | −65.61 |
| $v_3$ | Glyceraldehyde 3-P | 7.03 | 12.71 | 80.87 | 5.26 | −25.14 |
| $v_4$ | PEP | 14.05 | 25.42 | 80.87 | 10.52 | −25.14 |
| $v_5$ | Pyruvate | 13.12 | 24.12 | 83.81 | 10.09 | −23.13 |
| $v_6$ | Succinate* | 0.93 | 1.30 | 39.38 | 0.43 | −53.41 |
| $v_7$ | Lactate* | 2.57 | 0.60 | −76.76 | 0.17 | −93.48 |
| $v_8$ | Formate | 10.55 | 23.52 | 123.00 | 9.92 | −5.97 |
| $v_9$ | $H_2$* | 6.12 | 1.55 | −74.70 | 0.00 | −99.95 |
| $v_{RF}$ | Residual Formate* | 4.43 | 5.04 | 13.63 | 3.77 | −15.00 |
| $v_{10}$ | Ethanol* | 5.43 | 18.64 | 243.15 | 7.70 | 41.71 |
| $v_{11}$ | Acetate* | 5.12 | 4.88 | −4.59 | 2.22 | −56.59 |
| $v_{12}$ | New FDH Pathway+ | 0.00 | 16.94 | — | 6.15 | — |

TABLE 10

Anaerobic chemostat results.

| Strain | GJT001 (pDHK29) | GJT001 (pSBF2) | % Inc/Dec | BS1 (pSBF2) | % Inc/Dec |
|---|---|---|---|---|---|
| NADH | 6.64 | 6.40 | −3.60 | 5.53 | −16.70 |
| NAD+ | 6.27 | 5.90 | −5.95 | 4.34 | −30.74 |
| NADH/NAD+ | 1.06 | 1.09 | 2.74 | 1.29 | 21.42 |
| Total NAD(H/+) | 12.90 | 12.29 | −4.74 | 9.87 | −23.52 |
| $(R_{NADH})_f$ | 14.05 | 42.35 | — | 16.67 | — |
| $(R_{NADH})_u$ | 15.30 | 40.47 | — | 16.43 | — |
| $(NADH)_U/Gl$ | 1.96 | 3.13 | 59.69 | 2.97 | 51.53 |

Example 14

NADH/NAD+ Ratio

Importantly, the effect of the cofactor manipulations is smaller under chemostat conditions as compared to previous findings in anaerobic tube experiments (Et/Ac=27.0 for BS1 (pSBF2)). This is explained by the difference in the growth environment and conditions the cells are exposed to in a batch versus chemostat cultivation. In a chemostat bioreactor the specific growth rate equals the dilution rate, is fixed externally and is dependent on the strain and media composition for a batch culture. In addition, the transient nature of the batch cultivation implies that the concentration of both substrates and metabolites varies constantly with time, while at steady state these concentrations are time-invariant for a chemostat culture. Specifically, the cells are exposed to a very rich environment for most of the time during batch cultivation, while they are always under limiting environment under a chemostat setting. A similar behavior was observed previously in experiments where a significant acetate reduction was achieved under batch conditions by modulating glucose uptake using a glucose analog supplementation strategy, however the effect was greatly minimized under chemostat conditions (Chou et al., 1994).

The current results support previous findings (San et al., 2001) that the cell adjusts its partitioning at the acetyl-CoA node by changing the ethanol (consumes 2 NADH) to acetate (consumes no NADH) ratio to achieve a redox balance. Therefore, a change in the ethanol to acetate ratio (Et/Ac) is used as an indirect indicator of a change in the NADH/NAD+ ratio.

In the chemostat experiments, the NADH/NAD+ ratio increased slightly in strain BS1 (pSBF2), and it remained relatively unchanged for GJT001 (pSBF2) as compared to GJT001 (pDHK29). These results suggest that the cells regenerate the extra reducing power in the form of NADH that was available from the overexpression of the new FDH by increasing the flux to ethanol, which consumes 2 NADH, instead of accumulating the NADH as such. These findings might indicate that the NADH/NAD+ ratio is not always a good indicator of the oxidation state of the cell because in an effort to achieve a redox balance, the turnover is fast. This idea is supported by the fact that more than 96% of the NADH formed through the oxidation of glucose and the new FDH degradation pathway, $(R_{NADH})_f$, can be accounted for as being utilized for the formation of reduced metabolites, namely, succinate, lactate, and ethanol, $(R_{NADH})_U$ (Table 10). In addition, the specific NADH formation and utilization rates for both strains containing the new FDH are significantly higher than those of the control strain (Table 10).

Example 15

Effect of Redistributing Metabolic Flux

An analysis of the metabolic fluxes of the two experimental strains relative to the control strain shows a significant increase in the flux to ethanol, accompanied by a decrease in the flux to acetate and a marked decrease in the flux to lactate. The increase in the ethanol flux (2 NADH) in combination with the decrease in the flux to lactate (1 NADH) indicate that when there is an excess of reducing equivalents, ethanol formation is preferred since it provides a faster route to NAD+ regeneration. These results are in agreement with our previous findings in chemostat experiments utilizing carbon sources with different oxidation state (San et al., 2001). In those experiments, the lactate flux was highest for gluconate, a more oxidized carbon source, and lowest for sorbitol, a more reduced carbon source relative to glucose.

Figure 9:
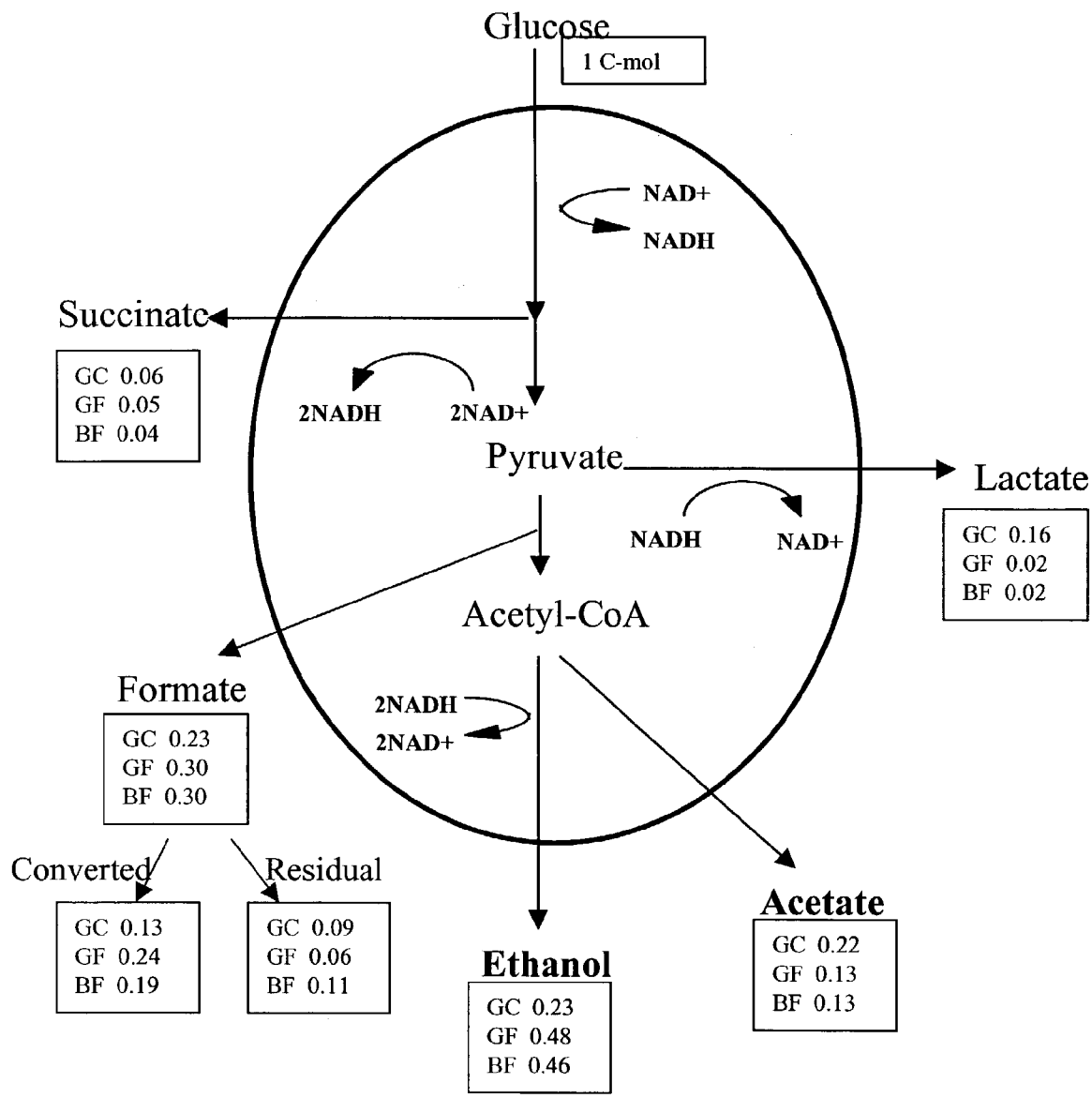
FIG. 9. Diagram showing the uptake of 1 C-mole of glucose in a cell together with yields of reduced products obtained in an anaerobic chemostatic experiment.

In addition, Table 9 presents the flux of formate converted to $CO_2$ through both the native FDH pathway ($v_9$) and the new NAD+-dependent FDH pathway ($v_{12}$) for the different strains. The flux to formate was obtained based on the assumption that one mole of formate is produced per mole of acetyl-CoA formed through the PFL pathway (FIG. 9). Therefore, the flux to formate ($v_8$) was calculated by adding the fluxes to ethanol ($v_{10}$) and acetate ($v_{11}$) from acetyl-CoA. The total formate converted was calculated by subtracting the measured residual formate flux ($v_{RF}$) from the flux to formate ($v_8$). The flux through the new FDH pathway ($v_{12}$) for strain GJT001 (pSBF2) was determined by subtracting the flux to $H_2$ ($v_9$), determined from GC measurements, from the total formate converted.

The absence of $H_2$ production as determined by GC analysis of the off-gases (Tables 7 and 8) confirmed the lack of native formate dehydrogenase activity in strain BS1 (pSBF2). For strain GJT001 (pSBF2), in which both FDH enzymes are active, 92% of the total formate converted to $CO_2$ was degraded through the NAD+-dependent FDH pathway. This result indicates that the new FDH enzyme competes very effectively with the native FDH for the available formate. This finding is consistent with the reported Km value for formate of the native FDH being twice (26 mM) that of the NAD+-dependent FDH (13 mM) (Schutte et al., 1976; Axley and Grahame, 1991).

Coexpression of both FDH enzymes in strain GJT001 (pSBF2) increased glucose uptake under chemostat conditions relative to the control strain. However, a decrease in glucose uptake was observed under the same conditions for strain BS1 (pSBF2). Due to the difference observed in glucose uptake, the yields in carbon-mole produced per carbon-mole of glucose consumed were calculated for the different metabolites. This allows a better understanding of how one carbon-mole (C-mole) of glucose consumed by the cell is distributed to the production of the different metabolites in each of the strains studied.

Example 16

Effect on Fermentation Products

The calculated yields for the different fermentation products are given in C-mole produced per C-mole of glucose consumed on FIG. 9. Values shown are yields in C-mole produced per C-mole of glucose consumed. The strains are identified as follows: GC=GJT001 (pDHK29), GF=GJT001 (pSBF2), and BF=BS1 (pSBF2). Results were obtained from anaerobic chemostat experiments at a dilution rate of 0.2 hr$^{-1}$. Unexpectedly, the percentage of carbon recovery obtained without accounting for the biomass was 90% or higher for all the strains.

For the control strain GJT001 (pDHK29), one C-mole of glucose is distributed almost equally to ethanol (0.23), acetate (0.22), and formate (0.23). The rest of it goes mostly to lactate (0.16), with succinate (0.06) being only a minor product. In contrast, for the strains containing the new FDH pathway, almost half of each C-mole of glucose was directed towards ethanol production (GJT001 (pSBF2): 0.48, BS1 (pSBF2): 0.46), while the yield to acetate decreased to 0.13, and that of formate increased (0.30) for both strains. At the same time, lactate proportion decreased to that of a minor product with a yield as low as 0.02. This yield is even lower than the yield of succinate, which remained relatively unchanged. It is important to note that the distribution of C-mole yields for strains GJT001 (pSBF2) and BS1 (pSBF2) is almost identical. This finding implies that under the experimental conditions studied the native FDH does not interfere with the action of the new FDH of redistributing the metabolic fluxes on a C-mole basis.

FIG. 9 also shows the amount of formate produced that is converted through either one or both of the FDH pathways. For the control strain, 57% of the formate produced is converted, while 80% is converted for GJT001 (pSBF2) and 63% for BS1 (pSBF2). These results show an increase in the conversion of formate with the overexpression of the new FDH, further suggesting that the new FDH has higher activity or higher affinity for formate than the native cofactor independent FDH.

Example 17

Recombinant FDH Competes with Native FDH

The reductive capabilities of the chemostat cultures further demonstrate an increase in the availability of intracellular NADH through metabolic engineering and therefore provide a more reduced environment under anaerobic chemostat conditions. The substitution of the native cofactor independent FDH pathway by the NAD+-dependent FDH provoked a significant redistribution of both metabolic fluxes and C-mole yields under anaerobic chemostat conditions.

The increased NADH availability favored the production of more reduced metabolites, as evidenced by a 3 to 4-fold increase in the ethanol to acetate ratio for BS1 (pSBF2) and GJT001 (pSBF2) as compared to the GJT1 (pDHK29) control. This was the result of an increase in the ethanol yield combined with a decrease in the acetate yield. It was also observed that the flux to lactate was reduced significantly with the overexpression of the new FDH.

In addition, the chemostat results suggest that the new FDH is able to compete very effectively with the native FDH; therefore, it is not necessary to eliminate the native FDH activity in order to achieve the desired results, making this approach easier to implement in a variety of applications. It should also be noted that the effect of this system was reduced under the current experimental conditions as compared to the uncontrolled anaerobic tube experiments reported previously, in which the Et/Ac ratio represented a 27-fold increase with substitution of the native by the NAD+-dependent FDH (see FIG. 4B).

Thus, the data demonstrate that NADH manipulations in a system comprising a NADH recycling system achieve redirection of carbon fluxes to produce reduced products. Based on this data, effects on other reduced cofactors such as FADH or NADPH directly are expected because of interconversions among the reduced cofactors in the cell. This reasoning leads to a plausible application of the present invention in terms of manipulating intracellular availability of other reduced cofactors such as FADH, a flavin coenzyme that is usually tightly bound to one particular enzyme, and NADPH, a nicotinamide cofactor that like NADH acts as a hydrogen carrier and is capable of diffusing from enzyme to enzyme.

Example 18

NADH Recycling in Biodesulfurization

The usual model for the study of biodesulfurization is the compound dibenzothiophene. It has been extensively studied in the context of nonbiological and biological desulfurization. Dibenzothiophene is a member of a class of polyaromatic sulfur heterocycles (PASHs), and one of thousands of PASHs found in a hydrotreated diesel sample. Alkylated dibenzothiophenes are also target molecules for biodesulfurization technology.

Cells capable of biodesulfurization are transformed with a recombinant NADH recycling system.

Known bacterial strains which are capable of breaking down dibenzothiophene using this pathway include *Rhodococcus* strains IGTS8, T09, and RA-18, and *Gordonia desulfuricans* 213E. Also capable of biodesulfurization are *E. coli* that express recombinant genes from *Rhodococcus*, and *Pseudomonas putida* that express recombinant genes from *Rhodococcus*. *Gordonia rubropertinctus* strain T08 is capable of biodesulfurization using a novel pathway.

The first step in the desulfurization pathway is the transfer of the target molecules from oil into the cells. *Rhodococcus* sp. and other bacteria have been shown to metabolize many insoluble molecules through direct transfer from oil into the cells.

Dibenzothiophene monooxygenase (SEQ ID NO:12, Accession NO: P54995), the enzyme responsible for the first two oxidation in the biodesulfurization pathway has been isolated and characterized, and its gene has been cloned and sequenced. The enzyme catalyzes the transfer of an electron from flavin mononucleotide to dibenzothiophene, and catalyzes the oxidation of dibenzothiophene to the sulfoxide and the oxidation of the sulfoxide to the sulfone. The cleavage of the first carbon-sulfur linkage of dibenzothiophene is catalyzed by dibenzothiophene sulfone monooxygenase (SEQ ID NO:13, Accession NO: P54997). This enzyme and its gene have been characterized. Production of sulfite is the last reaction in the pathway. This is catalyzed by a desulfinase (SEQ ID NO:14, Accession NO: P54998), whose gene has been cloned and sequenced. Sulfite is released as well as an oil soluble product, hydroxyl biphenyl.

NADH is required in this reaction system to keep the supply of reduced flavin mononucleotide in balance.

Additionally, large-scale biodesulfurization in bacteria utilizing recombinant, constitutively-expressed members of biodesulfurization pathway (dsz class genes), requires NADH, which can be limiting.

Example 19

NADH Recycling in Biopolymer Production

Polyhydroxyalkanoates (PHAs) are linear polyesters produced in nature in bacteria. Bacteria accumulate PHAs when a carbon source is abundant. The genes involved in PHA synthesis from well over 20 different microorganisms have been characterized. These recombinant genes are transformed into cells comprising the NADH recycling system. The genes involved in PHA synthesis include beta-ketothiolase, acetoacetyl-CoA-reductase, butyrate dehydrogenase and poly-3-hydroxybutyrate synthase.

Bacterial cells capable of PHA synthesis include the carbon monoxide (CO)-resistant strain of the hydrogen bacteria *Ralstonia eutropha* B5786, *Synechocystis* sp. PCC6803, and *Pseudomonas corrugata*. These bacteria are transformed with a recombinant NADH recycling system.

NADH recycling allows increased polymer production.

Example 20

NADH Recycling in Polypeptide Production

Cells comprising the NADH recycling system are transformed with a vector pSM552-545C-, containing the lacZ gene, which encodes beta-galactosidase. The expression of the lacZ gene is regulated by a powerful pH-inducible promoter. Experiments are conducted in a well-controlled fermenter under optimal conditions for the particular expression system. The expression of the lacZ gene is induced by changing the pH from 7.5, which has minimal induction, to a pH of 6.0, which is the optimal induction pH. NADH, acetate, and beta-galactosidase production are monitored through standard means in the art. Increased beta-galactosidase production is associated with lower levels of acetate. Lower levels of acetate production are associated with cells comprising the NADH recycling system.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Patents

U.S. Pat. No. 6,001,590
U.S. Pat. No. 5,264,092
U.S. Pat. No. 5,520,786
U.S. Pat. No. 5,393,615
U.S. Pat. No. 4,683,202
U.S. Pat. No. 5,928,906
U.S. Pat. No. 5,925,565
U.S. Pat. No. 5,935,819
U.S. Pat. No. 5,871,986
U.S. Pat. No. 4,879,236
U.S. Pat. No. 4,237,224
U.S. Pat. No. 5,783,681
U.S. Pat. No. 5,264,092
U.S. Pat. No. 5,705,629
U.S. Pat. No. 4,682,195
U.S. Pat. No. 5,645,897
U.S. Pat. No. 6,337,204
EP 266032

Publications

Alam, K. Y. and Clark, D. P. (1989). Anaerobic Fermentation Balance of *Escherichia coli* as Observed by *In vivo* Nuclear Magnetic Resonance Spectroscopy. *J. Bacteriol.* 171, 6213-6217.

Aristidou, A. A., San, K.-Y. and Bennett, G. N. (1995). Metabolic Engineering of *Escherichia coli* to Enhance Recombinant Protein Production through Acetate Reduction. *Biotech. Prog.* 11, 475-478.

Aristidou, A. A., San, K.-Y. and Bennett, G. N. (1999). Metabolic flux analysis of *Escherichia coli* expressing the *Bacillus subtilis* Acetolactate Synthase in Batch and Continuous Cultures. *Biotech. Bioeng.* 63, 737-749.

Axley, M. J. and Grahame, D. A. (1991). Kinetics for formate dehydrogenase of *Escherichia coli* formate-hydrogenlyase. *J. Biol. Chem.* 266, 13731-13736.

Baldoma, L. and Aguilar, J. (1988). Metabolism of L-fucose and L-rhamnose in *Escherichia coli*: aerobic-anaerobic regulation of L-lactaldegyde dissimilation. *J. Biotechnol.* 170, 416-421.

Bernofsky, C. and Swan, M. (1973). An Improved Cycling Assay for Nicotinamide Adenine Dinucleotide. *Anal. Biochem.* 53, 452-458.

Berrios-Rivera, S. J. (2000). Metabolic Engineering of Cofactors (NADH/NAD+) in *Escherichia coli*. In "Chemical Engineering". Rice University, Houston, Tex.

Berrios-Rivera, S. J., Bennett, G. N. and San, K.-Y. (2001). Metabolic Engineering of *Escherichia coli* Through Genetic Manipulation of NADH Availability. *Metabolic Eng.* (submitted).

Berrios-Rivera, S. J., Yang, Y.-T., San, K.-Y. and Bennett, G. N. (2000). Effect of Glucose Analog Supplementation in Anaerobic Chemostat Cultures of *Escherichia coli*. *Metabolic Eng.* 2, 149-154.

Chou, C.-H., Bennett, G. N. and San, K.-Y. (1994). Effect of Modulated Glucose Uptake on High-Level Recombinant Protein Production in a Dense *Escherichia coli* Culture. *Biotech. Prog.* 10, 644-647.

Foster, J. W., Park, Y. K., Penfound, T., Fenger, T. and Spector, M. P. (1990). Regulation of NAD Metabolism in *Salmonella typhimurium*: Molecular Sequence Analysis of the Bifunctional nadR Regulator and the nadA-pnuC Operon. *J. Bacteriol.* 172, 4187-4196.

Galkin, A., Kulakova, L., Yoshimura, T., Soda, K. and Esaki, N. (1997). Synthesis of Optically Active Amino Acids from α-Keto Acids with *Escherichia coli* Cells Expressing Heterologous Genes. *App. Environ. Microbiol.* 63, 4651-4656.

Graef, M. R., Alexeeva, S., DeSnoep, J. L. and Mattos, M. J. T. d. (1999). The Steady-State Internal Redox State (NADH/NAD) Reflects the External Redox State and Is Correlated with Catabolic Adaptation in *Escherichia coli*. *J. Bacteriol.* 181, 2351-2357.

Hummel, H. and Kula, M.-R. (1989). Dehydrogenases for the synthesis of chiral compounds. *Eur. J Biochem.* 184, 1-13.

Ingram, L. O. and Conway, T. (1988). Expression of Different Levels of Ethanologenic Enzymes from *Zymomonas mobilis* in Recombinant Strains of *Escherichia coli*. *App. Environ. Microbiol.* 54, 397-404.

Kragl, U., Kruse, W., Hummel, W. and Wandrey, C. (1996). Enzyme Engineering Aspects of Biocatalysis: Cofactor Regeneration as Example. *Biotech. Bioeng.* 52, 309-319.

Leonardo, M. R., Cunningham, P. R. and Clark, D. P. (1993). Anaerobic Regulation of the adhE Gene, Encoding the Fermentative Alcohol Dehydrogenase of *Escherichia coli*. *J. Bacteriol.* 175, 870-878.

Leonardo, M. R., Dailly, Y. and Clark, D. P. (1996). Role of NAD in regulating the adhE gene of *Escherichia coli*. *J. Bacteriol.* 178, 6013-6018.

Lopez de Felipe, F., Kleerebezem, M., Vos, W. M. d. and Hugenholtz, J. (1998). Cofactor Engineering: a Novel Approach to Metabolic Engineering in *Lactococcus lactis* by Controlled Expression of NADH Oxidase. *J. Bacteriol.* 180, 3804-3808.

Mandrand-Berthelot, M.-A., Wee, M. Y. K. and Haddock, B. A. (1978). An Improved Method for the Identification and Characterization of Mutants of *Escherichia coli* Deficient in Formate Dehydrogenase Activity. FEMS *Microbiol. Let.* 4, 37-40.

Maniatis, T., Fritsch, E. F. and Sambrook, J. (1989)."Molecular cloning: a laboratory manual," pp. Cold Spring Harbor Laboratory, Cold Spring Harbor, N.Y.

Park, D. H. and Zeikus, J. G. (1999). Utilization of Electrically Reduced Neutral Red by Actinobacillus succinogenes: Physiological Function of Neutral Red in Membrane-Driven Fumarate Reduction and Energy Conservation. *J. Bacteriol.* 181, 2403-2410.

Pecher, A., Zinoni, F., Jatisatienr, C., Wirth, R., Hennecke, H. and Bock, A. (1983). On the redox control of synthesis of anaerobically induced enzymes in enterobacteriaceae. *Arch. Microbiol.* 136, 131-136.

Phillips, G. J., Park, S.-K. and Huber, D. (2000). High Copy Number Plasmids Compatible with Commonly Used Cloning Vectors. *BioTechniques* 28, 400-408.

Riondet, C., Cachon, R., Wache, Y., Alraraz, G. and Divies, C. (2000). Extracellular Oxidoreduction Potential Modifies Carbon and Electron Flow in *Escherichia coli*. *J. Bacteriol.* 182, 620-626.

Sakai, Y., Murdanoto, A. P., Konishi, T., Iwamatsu, A. and Kato, N. (1997). Regulation of the Formate Dehydrogenase Gene, FDH1, in the Methylotrophic Yeast *Candida boidinii* and Growth Characteristics of an FDH1-Disrupted Strain on Methanol, Methylamine and Choline. *J. Bacteriol.* 179, 4480-4485.

San, K.-Y., Bennett, G. N., Berrios-Rivera, S. J., Vadali, R., Sariyar, B. and Blackwood, K. (2001). Metabolic engineering through cofactor manipulation and its effects on metabolic flux redistribution in *Escherichia coli*. (Submitted)

Schutte, H., Flossdorf, J., Sahm, H. and Kula, M.-R. (1976). Purification and Properties of Formaldehyde Dehydrogenase and Formate Dehydrogenase from *Candida boidinii*. *Eur. J Biochem.* 62, 151-160.

Tishkov, V. I., Galkin, A. G., Fedorchuk, V. V., Savitsky, P. A., Rojkova, A. M., Gieren, H. and Kula, M. R. (1999). Pilot scale production and isolation of recombinant NAD+- and NADP+-specific formate dehydrogenases. *Biotech. Bioeng.* 64, 187-93.

Tolentino, G. J., Meng, S.-Y., Bennett, G. N. and San, K.-Y. (1992). A pH-regulated promoter for the expression of recombinant proteins in *Escherichia coli*. *Biotech. Let.* 14, 157-162.

Wimpenny, J. W. T. and Firth, A. (1972). Levels of Nicotinamide Adenine Dinucleotide and Reduced Nicotinamide Adenine Dinucleotide in Facultative Bacteria and the Effect of Oxygen. *J. Bacteriol.* 111, 24-32.

Yang, Y.-T., Aristidou, A. A., San, K.-Y. and Bennett, G. N. (1999). Metabolic flux analysis of *Escherichia coli* deficient in the acetate production pathway and expressing the *Bacillus subtilis* acetolactate synthase. *Metabolic Eng.* 1, 26-34.

Zinoni, F., Birkmann, A., Stadtman, T. and Bock, A. (1986). Nucleotide sequence and expression of the selenocysteine-containing polypeptide of formate dehydrogenase (formate-hydrogen-lyase-linked) from *Escherichia coli*. *Proc. Nat. Acad. Sci.* 83, 4650-4.

One skilled in the art readily appreciates that the present invention is well adapted to carry out the objectives and obtain the ends and advantages mentioned as well as those inherent therein. Systems, pharmaceutical compositions, treatments, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

What is claimed is:

1. An isolated engineered cell, comprising a recombinant NADH-recycling system having:
   (a) a native cofactor-independent formate dehydrogenase genetically engineered to reduce its enzymatic activity as compared with the activity in a non-engineered cell, and
   (b) an expression construct comprising an expressible gene encoding a heterologous NAD+-dependent formate dehydrogenase (FDH) that increases the enzymatic activity of NAD+-dependent FDH in the cell as compared with the activity of NAD+-dependent FDH in a non-engineered cell,
   wherein said FDH converts NAD+ to NADH in the presence of formate.

2. The cell of claim 1, wherein said cofactor-independent formate dehydrogenase is engineered to eliminate its activity by deletion, inactivation, or mutation.

3. The cell of claim 2, wherein said heterologous FDH is selected from the group consisting of *Candida boidinii* FDH, *Candida methylica* FDH, *Pseodomonas* sp 101 FDH, *Arabidopsis thaliana* FDH, *Staphylococcus aureus* FDH, *Saccharomyces bayanus* FDH, *Saccharomyces exiguus* FDH, *Saccharomyces servazzii* FDH, *Zygosaccharomyces rouxil* FDH, *Saccharomyces kluyveri* FDH, *Kluyveromyces thermotolerans* FDH, *Kluyveromyces lactis* FDH, *Kluyveromyces marxianus* FDH, *Pichia angusta* FDH, *Debaryomyces hansenii* FDH, *Pichia sorbitophila* FDH, *Candida tropicalis* FDH, and *Yarrowia lipolytica* FDH.

4. The cell of claim 3, wherein said FDH comprises a sequence selected from the group consisting of SEQ ID NO: 2, SEQ ID NO: 3, SEQ ID NO: 4, SEQ ID NO: 5, and SEQ ID NO: 6.

5. An isolated engineered bacterial cell with a recombinant NADH-recycling system comprising:
   (a) a native cofactor-independent formate dehydrogenase that has been inactivated by mutation or deletion, and
   (b) an expression construct comprising an expressible gene encoding a heterologous NAD+-dependent formate dehydrogenase (FDH) that results in overexpression of the NAD+-dependent FDH as compared with the expression of NAD+-dependent FDH in a non-engineered cell, wherein said FDH converts NAD+ to NADH in the presence of formate.

6. The bacterial cell of claim 5, wherein said heterologous FDH is selected from the group consisting of *Candida boidinii* FDH, *Candida methylica* FDH, *Pseodomonas* sp 101 FDH, *Arabidopsis thaliana* FDH, *Staphylococcus aureus* FDH, *Saccharomyces bayanus* FDH, *Saccharomyces exiguus* FDH, *Saccharomyces servazzii* FDH, *Zygosaccharomyces rouxii* FDH, *Saccharomyces kluyveri* FDH, *Kluyveromyces thermotolerans* FDH, *Kluyveromyces lactis* FDH, *Kluyveromyces marxianus* FDH, *Pichia angusta* FDH, *Debaryomyces hansenii* FDH, *Pichia sorbitophila* FDH, *Candida tropicalis* FDH, and *Yarrowia lipolytica* FDH.

7. The bacterial cell of claim 6, wherein said FDH comprises a sequence selected from the group consisting of SEQ ID NO: 2, SEQ ID NO: 3, SEQ ID NO: 4, SEQ ID NO: 5, and SEQ ID NO: 6.

8. A bacterial cell comprising an expression vector encoding a heterologous NAD+-dependent formate dehydrogenase (FDH) and lacking cofactor-independent formate dehydrogenase activity, wherein said FDH converts NAD+ to NADH in the presence of formate.

* * * * *

UNITED STATES PATENT AND TRADEMARK OFFICE
CERTIFICATE OF CORRECTION

| | |
|---|---|
| PATENT NO. | : 7,256,016 B2 |
| APPLICATION NO. | : 10/286326 |
| DATED | : August 14, 2007 |
| INVENTOR(S) | : Ka-Yiu San, Susana J. Berrios-Rivera and George N. Bennett |

Page 1 of 1

It is certified that error appears in the above-identified patent and that said Letters Patent is hereby corrected as shown below:

Column 61 Line 32 to Line 33 - The genus species name "Zygosaccharomyces rouxil FDH" is misspelled and should be --Zygosaccharomyces rouxii FDH--.

Signed and Sealed this

Thirtieth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO.        : 7,256,016 B2                                                    Page 1 of 1
APPLICATION NO.   : 10/286326
DATED             : August 14, 2007
INVENTOR(S)       : Ka Yui San et al.

It is certified that error appears in the above-identified patent and that said Letters Patent is hereby corrected as shown below:

Column 1, Lines 9 to 11 - Replace the sentences "The present invention was developed with funds from the United States Government. Therefore, the United States Government may have certain rights in the invention." with -- This invention was made with government support under Grant Number BES-0000303 awarded by the National Science Foundation. The government has certain rights in the invention. --

Signed and Sealed this

Thirty-first Day of August, 2010

David J. Kappos
*Director of the United States Patent and Trademark Office*

SEQUENCE LISTING

```
<160> NUMBER OF SEQ ID NOS: 14

<210> SEQ ID NO 1
<211> LENGTH: 1562
<212> TYPE: DNA
<213> ORGANISM: Candida boidinii
```

-continued

```
<400> SEQUENCE: 1
ttcaactaaa aattgaacta tttaaacact atgatttcct tcaattatat taaaatcaat        60
ttcatatttc cttacttctt tttgctttat tatacatcaa taactcaatt aactcattga       120
ttatttgaaa aaaaaaaaca tttattaact taactccccg attatatatt atattattga       180
ctttacaaaa tgaagatcgt tttagtctta tatgatgctg gtaagcacgc tgctgatgaa       240
gaaaaattat atggttgtac tgaaaataaa ttaggtattg ctaattggtt aaaagatcaa       300
ggtcatgaac taattactac ttctgataaa gaaggtgaaa caagtgaatt ggataaacat       360
atcccagatg ctgatattat catcaccact cctttccatc ctgcttatat cactaaggaa       420
agacttgaca aggctaagaa cttaaaatta gtcgttgtcg ctggtgttgg ttctgatcac       480
attgatttag attatattaa tcaaacaggt aagaaaatct cagtcttgga agttacaggt       540
tctaatgttg tctctgttgc tgaacacgtt gtcatgacca tgcttgtctt ggttagaaat       600
ttcgttccag cacatgaaca aattattaac cacgattggg aggttgctgc tatcgctaag       660
gatgcttacg atatcgaagg taaaactatt gctaccattg gtgctggtag aattggttac       720
agagtcttgg aaagattact cccttttaat ccaaaagaat tattatacta cgattatcaa       780
gctttaccaa agaagctgag agaaaaagtt ggtgctagaa gagttgaaaa attgaagaa        840
ttagttgctc aagctgatat cgttacagtt aatgctccat acacgcagg tacaaaaggt         900
ttaattaata aggaattatt atctaaattt aaaaaaggtg cttggttagt caataccgca       960
agaggtgcta tttgtgttgc tgaagatgtt gcagcagctt tagaatctgg tcaattaaga      1020
ggttacggtg tgatgtttg gttcccacaa ccagctccaa aggatcaccc atggagagat       1080
atgagaaata aatatggtgc tggtaatgcc atgactcctc actactctgg tactactta       1140
gatgctcaaa caagatacgc tgaaggtact aaaaatatct tggaatcatt ctttactggt      1200
aaatttgatt acagaccaca agatattatc ttattaaatg gtgaatacgt tactaaagct      1260
tacggtaaac acgataagaa ataaatttc ttaacttgaa aactataatt gctataacaa       1320
ttcttcaatt tctcttttc ttcctttttt tgaagaattt ttaacaatca aaatttgac         1380
tctttgattt cccgcaatct ctgagctcag catactcatt attatttat tattattatt       1440
attattactt ttattattat tatattttty cttctttaac gatatcgttt gtgttttatc      1500
ttttatgatt taaattttat acgaatttat gaatacaaca aaatatttaa gtttacacaa      1560
tg                                                                    1562

<210> SEQ ID NO 2
<211> LENGTH: 364
<212> TYPE: PRT
<213> ORGANISM: Candida boidinii

<400> SEQUENCE: 2

Met Lys Ile Val Leu Val Leu Tyr Asp Ala Gly Lys His Ala Ala Asp
 1               5                  10                  15

Glu Glu Lys Leu Tyr Gly Cys Thr Glu Asn Lys Leu Gly Ile Ala Asn
             20                  25                  30

Trp Leu Lys Asp Gln Gly His Glu Leu Ile Thr Thr Ser Asp Lys Glu
         35                  40                  45

Gly Glu Thr Ser Glu Leu Asp Lys His Ile Pro Asp Ala Asp Ile Ile
     50                  55                  60

Ile Thr Thr Pro Phe His Pro Ala Tyr Ile Thr Lys Glu Arg Leu Asp
 65                  70                  75                  80
```

Lys Ala Lys Asn Leu Lys Leu Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
            115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360

<210> SEQ ID NO 3
<211> LENGTH: 364
<212> TYPE: PRT
<213> ORGANISM: Candida methylica

<400> SEQUENCE: 3

Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Ser Val Val Val Ala Gly Val Gly Ser Asp

```
                    85                  90                  95
His Ile Asp Leu Asp Tyr Ile Asn Gln Thr Gly Lys Lys Ile Ser Val
                100                 105                 110

Leu Glu Val Thr Gly Ser Asn Val Val Ser Val Ala Glu His Val Val
            115                 120                 125

Met Thr Met Leu Val Leu Val Arg Asn Phe Val Pro Ala His Glu Gln
130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360

<210> SEQ ID NO 4
<211> LENGTH: 401
<212> TYPE: PRT
<213> ORGANISM: Pseudomonas

<400> SEQUENCE: 4

Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Thr Leu Pro Thr Pro Lys Ala Ile Asp Phe Thr Pro Gly
        35                  40                  45

Gln Leu Leu Gly Ser Val Ser Gly Glu Leu Gly Leu Arg Lys Tyr Leu
    50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Val Ile Ser
                85                  90                  95
```

```
Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140

Tyr Cys Asn Ser Ile Ser Val Ala Glu His Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
                180                 185                 190

Met His Val Gly Thr Val Ala Ala Gly Arg Ile Gly Leu Ala Val Leu
            195                 200                 205

Arg Arg Leu Ala Pro Phe Asp Val His Leu His Tyr Thr Asp Arg His
210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
        290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
        355                 360                 365

Val Gln Gly Gly Ala Leu Ala Gly Thr Gly Ala His Ser Tyr Ser Lys
    370                 375                 380

Gly Asn Ala Thr Gly Gly Ser Glu Glu Ala Ala Lys Phe Lys Lys Ala
385                 390                 395                 400

Val

<210> SEQ ID NO 5
<211> LENGTH: 384
<212> TYPE: PRT
<213> ORGANISM: Arabidopsis thaliana

<400> SEQUENCE: 5

Met Ala Met Arg Gln Ala Ala Lys Ala Thr Ile Arg Ala Cys Ser Ser
1               5                   10                  15

Ser Ser Ser Ser Gly Tyr Phe Ala Arg Arg Gln Phe Asn Ala Ser Ser
            20                  25                  30

Gly Asp Ser Lys Lys Ile Val Gly Val Phe Tyr Lys Ala Asn Glu Tyr
        35                  40                  45

Ala Thr Lys Asn Pro Asn Phe Leu Gly Cys Val Glu Asn Ala Leu Gly
    50                  55                  60
```

```
Ile Arg Asp Trp Leu Glu Ser Gln Gly His Gln Tyr Ile Val Thr Asp
 65                  70                  75                  80

Asp Lys Glu Gly Pro Asp Cys Glu Leu Glu Lys His Ile Pro Asp Leu
                 85                  90                  95

His Val Leu Ile Ser Thr Pro Phe His Pro Ala Tyr Val Thr Ala Glu
            100                 105                 110

Arg Ile Lys Lys Ala Lys Asn Leu Lys Leu Leu Thr Ala Gly Ile
        115                 120                 125

Gly Ser Asp His Ile Asp Leu Gln Ala Ala Ala Ala Gly Leu Thr
130                 135                 140

Val Ala Glu Val Thr Gly Ser Asn Val Val Ser Val Ala Glu Asp Glu
145                 150                 155                 160

Leu Met Arg Ile Leu Ile Leu Met Arg Asn Phe Val Pro Gly Tyr Asn
                165                 170                 175

Gln Val Val Lys Gly Glu Trp Asn Val Ala Gly Ile Ala Tyr Arg Ala
            180                 185                 190

Tyr Asp Leu Glu Gly Lys Thr Ile Gly Thr Val Gly Ala Gly Arg Ile
        195                 200                 205

Gly Lys Leu Leu Leu Gln Arg Leu Lys Pro Phe Gly Cys Asn Leu Leu
    210                 215                 220

Tyr His Asp Arg Leu Gln Met Ala Pro Glu Leu Glu Lys Glu Thr Gly
225                 230                 235                 240

Ala Lys Phe Val Glu Asp Leu Asn Glu Met Leu Pro Lys Cys Asp Val
                245                 250                 255

Ile Val Ile Asn Met Pro Leu Thr Glu Lys Thr Arg Gly Met Phe Asn
            260                 265                 270

Lys Glu Leu Ile Gly Lys Leu Lys Lys Gly Val Leu Ile Val Asn Asn
        275                 280                 285

Ala Arg Gly Ala Ile Met Glu Arg Gln Ala Val Val Asp Ala Val Glu
    290                 295                 300

Ser Gly His Ile Gly Gly Tyr Ser Gly Asp Val Trp Asp Pro Gln Pro
305                 310                 315                 320

Ala Pro Lys Asp His Pro Trp Arg Tyr Met Pro Asn Gln Ala Met Thr
                325                 330                 335

Pro His Thr Ser Gly Thr Thr Ile Asp Ala Gln Leu Arg Tyr Ala Ala
            340                 345                 350

Gly Thr Lys Asp Met Leu Glu Arg Tyr Phe Lys Gly Glu Asp Phe Pro
        355                 360                 365

Thr Glu Asn Tyr Ile Val Lys Asp Gly Glu Leu Ala Pro Gln Tyr Arg
    370                 375                 380
```

<210> SEQ ID NO 6
<211> LENGTH: 374
<212> TYPE: PRT
<213> ORGANISM: Staphylococcus aureus

<400> SEQUENCE: 6

```
Met Ser Asn Gly Ala Val Phe Phe Val Ile Phe Leu Lys Gln Ala Thr
  1               5                  10                  15

Cys Asn Thr Tyr Phe Lys Glu Val Lys Ile Tyr His Leu Gly Glu Met
             20                  25                  30

Asp Met Lys Ile Val Ala Leu Phe Pro Glu Ala Val Glu Gly Gln Glu
         35                  40                  45

Asn Gln Leu Leu Asn Thr Lys Lys Ala Leu Gly Leu Lys Thr Phe Leu
```

```
                 50                 55                  60
Glu Glu Arg Gly His Glu Phe Ile Ile Leu Ala Asp Asn Gly Glu Asp
 65                  70                  75                  80

Leu Asp Lys His Leu Pro Asp Met Asp Val Ile Ile Ser Ala Pro Phe
                 85                  90                  95

Tyr Pro Ala Tyr Met Thr Arg Glu Arg Ile Glu Lys Ala Pro Asn Leu
                100                 105                 110

Lys Leu Ala Ile Thr Ala Gly Val Gly Ser Asp His Val Asp Leu Ala
                115                 120                 125

Ala Ala Ser Glu His Asn Ile Gly Val Val Glu Val Thr Gly Ser Asn
130                 135                 140

Thr Val Ser Val Ala Glu His Ala Val Met Asp Leu Leu Ile Leu Leu
145                 150                 155                 160

Arg Asn Tyr Glu Glu Gly His Arg Gln Ser Val Glu Gly Glu Trp Asn
                165                 170                 175

Leu Ser Gln Val Gly Asn His Ala His Glu Leu Gln His Lys Thr Ile
                180                 185                 190

Gly Ile Phe Gly Phe Gly Arg Ile Gly Gln Leu Val Ala Glu Arg Leu
                195                 200                 205

Ala Pro Phe Asn Val Thr Leu Gln His Tyr Asp Pro Ile Asn Gln Gln
210                 215                 220

Asp His Lys Leu Ser Lys Phe Val Ser Phe Asp Glu Leu Val Ser Thr
225                 230                 235                 240

Ser Asp Ala Ile Thr Ile His Ala Pro Leu Thr Pro Glu Thr Asp Asn
                245                 250                 255

Leu Phe Asp Lys Asp Val Leu Ser Arg Met Lys Lys His Ser Tyr Leu
                260                 265                 270

Val Asn Thr Ala Arg Gly Lys Ile Val Asn Arg Asp Ala Leu Val Glu
                275                 280                 285

Ala Leu Ala Ser Glu His Leu Gln Gly Tyr Ala Gly Asp Val Trp Tyr
290                 295                 300

Pro Gln Pro Ala Pro Ala Asp His Pro Trp Arg Thr Met Pro Arg Asn
305                 310                 315                 320

Ala Met Thr Val His Tyr Ser Gly Met Thr Leu Glu Ala Gln Lys Arg
                325                 330                 335

Ile Glu Asp Gly Val Lys Asp Ile Leu Glu Arg Phe Phe Asn His Glu
                340                 345                 350

Pro Phe Gln Asp Lys Asp Ile Ile Val Ala Ser Gly Arg Ile Ala Ser
                355                 360                 365

Lys Ser Tyr Thr Ala Lys
    370

<210> SEQ ID NO 7
<211> LENGTH: 2971
<212> TYPE: DNA
<213> ORGANISM: E. coli

<400> SEQUENCE: 7
gggcgctgcc ggcacctgtc ctacgagttg catgataaag aagacagtca taagtgcggc     60
gacgatagtc atgccccgcg cccaccggaa ggagctaccg gcagcggtgc ggactgttgt    120
aactcagaat aagaaatgag gccgctcatg gcgttggtct gaaattgccg ctgtttgacg    180
gtggacggtt gaatgccaat ctcgaaggca cgcgcgccgc cagcaacatg atgattgaac    240
gttacaacca gtcagtactg aacgcggtgc gtgacgttgc cgtcaacggc acgcgtctgc    300
```

```
aaacgctcaa cgacgagcga gaaatgcagg ctgaacgcgt ggaagccacg cgctttaccc    360
agcgcgctgc cgaggccgcc tatcagcgcg gcttaaccag ccgcttacag gccaccgaag    420
cccggttgcc agtgcttgcc gaagagatgt cattactgat gctggacagc cgccgggtga    480
tccaaagcat tcagttgatg aaatcgctgg gcggcgggta tcaggcaggt cccgtcgtcg    540
agaaaaaata aaatgtctgc cgcgtgatgg ctgtcacgcg gtatttcgtt tcgtcacgtc    600
aaaactgacg acagcctgtt tttcgtcaga gttttgaata aatagtgccc gtaatatcag    660
ggaatgaccc cacataaaat gtggcataaa agatgcatac tgtagtcgag agcgcgtatg    720
cgtgatttga ttaactggag cgagaccgat gaaaaaagtc gtcacggttt gcccctattg    780
cgcatcaggt tgcaaaatca acgtggtcgt cgataacggc aaaatcgtcc gggcggaggc    840
agcgcagggg aaaaccaacc agggtaccct gtgtctgaag ggttattatg ctgggactt     900 cattaacgat acccagatcc tgaccccgcg cctgaaaacc cccatgatcc gtcgccagcg    960
tggcggcaaa ctcgaacctg tttcctggga tgaggcactg aattacgttg ccgagcgcct   1020
gagcgccatc aaagagaagt acggtccgga tgccatccag acgaccggct cctcgcgtgg   1080
tacgggtaac gaaaccaact atgtaatgca aaaatttgcg cgcgccgtta ttggtaccaa   1140
taacgttgac tgctgcgctc gtgtctgaca cggcccatcg gttgcaggtc tgcaccaatc   1200
ggtcggtaat ggcgcaatga gcaatgctat taacgaaatt gataataccg atttagtgtt   1260
cgttttcggg tacaacccgg cggattccca cccaatcgtg gcgaatcacg taattaacgc   1320
taaacgtaac ggggcgaaaa ttatcgtctg cgatccgcgc aaaattgaaa ccgcgcgcat   1380
tgctgacatg cacattgcac tgaaaaacgg ctcgaacatc gcgctgttga atgcgatggg   1440
ccatgtcatt attgaagaaa atctgtacga caaagcgttc gtcgcttcac gtacagaagg   1500
ctttgaagag tatcgtaaaa tcgttgaagg ctacacgccg gagtcggttg aagatatcac   1560
cggcgtcagc gccagtgaga ttcgtcaggc ggcacggatg tatgcccagg cgaaaagcgc   1620
cgccatcctg tggggcatgg gtgtaaccca gttctaccag ggcgtggaaa ccgtgcgttc   1680
tctgaccagc ctcgcgatgc tgaccggtaa cctcggtaag ccgcatgcgg gtgttaaccc   1740
ggttcgtggt cagaacaacg ttcagggtgc ctgcgatatg ggcgcgctgc cggatacgta   1800
tccgggatac cagtacgtga agatccggc taaccgcgag aaattcgcca aagcctgggg   1860
cgtggaaagc ctgccagcgc ataccggcta tcgcatcagc gagctgccgc accgcgcagc   1920
gcatggcgaa gtcgtgccg cgtacattat gggcgaagat ccgctacaaa ctgacgcgga   1980
gctgtcggca gtacgtaaag cctttgaaga tctggaactg gttatcgttc aggacatctt   2040
tatgaccaaa accgcgtcgg cggcggatgt tattttaccg tcaacgtcgt ggggcgagca   2100
tgaaggcgtg tttactgcgg ctgaccgtgg cttccagcgt ttcttcaagg cggttgaacc   2160
gaaatgggat ctgaaaacgg actggcaaat catcagtgaa atcgccaccc gtatgggtta   2220
tccgatgcac tacaacaaca cccaggagat ctgggatgag ttcgtcatcc tgtgcccgga   2280
tttctacggt gcgacttacg agaaaatggg cgaactgggc ttcattcagt ggccttgccg   2340
cgatacttca gatgccgatc aggggacttc ttatctgttt aaagagaagt tgataccccc   2400
gaacggtctg cgcagttct tcacctgcga ctgggtagcg ccaatcgaca aactcaccga   2460
cgagtacccg atggtactgt caacggtgcg tgaagttggt cactactctt gccgttcgat   2520
gaccggtaac tgtgcggcac tggcggcgct ggctgatgaa cctggctacg cacaaatcaa   2580
taccgaagac gccaaacgtc tgggtattga agatgaggca ttggtttggg tgcactcgcg   2640
```

-continued taaaggcaaa attatcaccc gtgcgcaggt cagcgatcgt ccgaacaaag gggcgattta 2700
catgacctac cagtggtgga ttggtgcctg taacgagctg gttaccgaaa acttaagccc 2760
gattacgaaa acgccggagt acaaatactg cgccgttcgc gtcgagccga tcgccgatca 2820
gcgcgccgcc gagcagtacg tgattgacga gtacaacaag ttgaaaactc gcctgcgcga 2880
agcggcactg gcgtaatacc gtcctttcta cagcctcctt tcggaggctg ttttttttatc 2940 cattcgaact ctttatactg gttacttccc g 2971

<210> SEQ ID NO 8
<211> LENGTH: 19
<212> TYPE: DNA
<213> ORGANISM: Artificial Sequence
<220> FEATURE:
<223> OTHER INFORMATION: PRIMER

<400> SEQUENCE: 8
gattaactgg agcgagacc                                            19

<210> SEQ ID NO 9
<211> LENGTH: 18
<212> TYPE: DNA
<213> ORGANISM: Artificial Sequence
<220> FEATURE:
<223> OTHER INFORMATION: PRIMER

<400> SEQUENCE: 9
tccgaaagga ggctgtag                                             18

<210> SEQ ID NO 10
<211> LENGTH: 53
<212> TYPE: DNA
<213> ORGANISM: artificial sequence
<220> FEATURE:
<223> OTHER INFORMATION: PRIMER

<400> SEQUENCE: 10
gcggaattca ggaggaattt aaaatgaaga tcgtttttagt cttatatgat gct        53

<210> SEQ ID NO 11
<211> LENGTH: 36
<212> TYPE: DNA
<213> ORGANISM: Artificial Sequence
<220> FEATURE:
<223> OTHER INFORMATION: PRIMER

<400> SEQUENCE: 11
cgcggatcct tatttcttat cgtgtttacc gtaagc                          36

<210> SEQ ID NO 12
<211> LENGTH: 453
<212> TYPE: PRT
<213> ORGANISM: Rhodococcus

<400> SEQUENCE: 12

Met Thr Gln Gln Arg Gln Met His Leu Ala Gly Phe Phe Ser Ala Gly
1               5                   10                  15

Asn Val Thr His Ala His Gly Ala Trp Arg His Thr Asp Ala Ser Asn
                20                  25                  30

Asp Phe Leu Ser Gly Lys Tyr Tyr Gln His Ile Ala Arg Thr Leu Glu
        35                  40                  45

Arg Gly Lys Phe Asp Leu Leu Phe Leu Pro Asp Gly Leu Ala Val Glu
    50                  55                  60

```
Asp Ser Tyr Gly Asp Asn Leu Asp Thr Gly Val Gly Leu Gly Gly Gln
 65                  70                  75                  80

Gly Ala Val Ala Leu Glu Pro Ala Ser Val Val Ala Thr Met Ala Ala
                 85                  90                  95

Val Thr Glu His Leu Gly Leu Gly Ala Thr Ile Ser Ala Thr Tyr Tyr
            100                 105                 110

Pro Pro Tyr His Val Ala Arg Val Phe Ala Thr Leu Asp Gln Leu Ser
            115                 120                 125

Gly Gly Arg Val Ser Trp Asn Val Val Thr Ser Leu Asn Asp Ala Glu
            130                 135                 140

Ala Arg Asn Phe Gly Ile Asn Gln His Leu Glu His Asp Ala Arg Tyr
145                 150                 155                 160

Asp Arg Ala Asp Glu Phe Leu Glu Ala Val Lys Lys Leu Trp Asn Ser
                165                 170                 175

Trp Asp Glu Asp Ala Leu Val Leu Asp Lys Ala Ala Gly Val Phe Ala
            180                 185                 190

Asp Pro Ala Lys Val His Tyr Val Asp His His Gly Glu Trp Leu Asn
            195                 200                 205

Val Arg Gly Pro Leu Gln Val Pro Arg Ser Pro Gln Gly Glu Pro Val
210                 215                 220

Ile Leu Gln Ala Gly Leu Ser Pro Arg Gly Arg Arg Phe Ala Gly Lys
225                 230                 235                 240

Trp Ala Glu Ala Val Phe Ser Leu Ala Pro Asn Leu Glu Val Met Gln
                245                 250                 255

Ala Thr Tyr Gln Gly Ile Lys Ala Glu Val Asp Ala Ala Gly Arg Asp
            260                 265                 270

Pro Asp Gln Thr Lys Ile Phe Thr Ala Val Met Pro Val Leu Gly Glu
            275                 280                 285

Ser Gln Ala Val Ala Gln Glu Arg Leu Glu Tyr Leu Asn Ser Leu Val
290                 295                 300

His Pro Glu Val Gly Leu Ser Thr Leu Ser Ser His Thr Gly Ile Asn
305                 310                 315                 320

Leu Ala Ala Tyr Pro Leu Asp Thr Pro Ile Lys Asp Ile Leu Arg Asp
                325                 330                 335

Leu Gln Asp Arg Asn Val Pro Thr Gln Leu His Met Phe Ala Ala Ala
            340                 345                 350

Thr His Ser Glu Glu Leu Thr Leu Ala Glu Met Gly Arg Arg Tyr Gly
            355                 360                 365

Thr Asn Val Gly Phe Val Pro Gln Trp Ala Gly Thr Gly Glu Gln Ile
370                 375                 380

Ala Asp Glu Leu Ile Arg His Phe Glu Gly Ala Ala Asp Gly Phe
385                 390                 395                 400

Ile Ile Ser Pro Ala Phe Leu Pro Gly Ser Tyr Asp Glu Phe Val Asp
                405                 410                 415

Gln Val Val Pro Val Leu Gln Asp Arg Gly Tyr Phe Arg Thr Glu Tyr
            420                 425                 430

Gln Gly Asn Thr Leu Arg Asp His Leu Gly Leu Arg Val Pro Gln Leu
            435                 440                 445

Gln Gly Gln Pro Ser
    450

<210> SEQ ID NO 13
<211> LENGTH: 365
```

```
<212> TYPE: PRT
<213> ORGANISM: Rhodococcus

<400> SEQUENCE: 13

Met Thr Ser Arg Val Asp Pro Ala Asn Pro Gly Ser Glu Leu Asp Ser
1               5                   10                  15

Ala Ile Arg Asp Thr Leu Thr Tyr Ser Asn Cys Pro Val Pro Asn Ala
            20                  25                  30

Leu Leu Thr Ala Ser Glu Ser Gly Phe Leu Asp Ala Ala Gly Ile Glu
        35                  40                  45

Leu Asp Val Leu Ser Gly Gln Gln Gly Thr Val His Phe Thr Tyr Asp
50                  55                  60

Gln Pro Ala Tyr Thr Arg Phe Gly Gly Glu Ile Pro Pro Leu Leu Ser
65                  70                  75                  80

Glu Gly Leu Arg Ala Pro Gly Arg Thr Arg Leu Leu Gly Ile Thr Pro
                85                  90                  95

Leu Leu Gly Arg Gln Gly Phe Phe Val Arg Asp Asp Ser Pro Ile Thr
            100                 105                 110

Ala Ala Ala Asp Leu Ala Gly Arg Arg Ile Gly Val Ser Ala Ser Ala
        115                 120                 125

Ile Arg Ile Leu Arg Gly Gln Leu Gly Asp Tyr Leu Glu Leu Asp Pro
130                 135                 140

Trp Arg Gln Thr Leu Val Ala Leu Gly Ser Trp Glu Ala Arg Ala Leu
145                 150                 155                 160

Leu His Thr Leu Glu His Gly Glu Leu Gly Val Asp Asp Val Glu Leu
                165                 170                 175

Val Pro Ile Ser Ser Pro Gly Val Asp Val Pro Ala Glu Gln Leu Glu
            180                 185                 190

Glu Ser Ala Thr Val Lys Gly Ala Asp Leu Phe Pro Asp Val Ala Arg
        195                 200                 205

Gly Gln Ala Ala Val Leu Ala Ser Gly Asp Val Asp Ala Leu Tyr Ser
210                 215                 220

Trp Leu Pro Trp Ala Gly Glu Leu Gln Ala Thr Gly Ala Arg Pro Val
225                 230                 235                 240

Val Asp Leu Gly Leu Asp Glu Arg Asn Ala Tyr Ala Ser Val Trp Thr
                245                 250                 255

Val Ser Ser Gly Leu Val Arg Gln Arg Pro Gly Leu Val Gln Arg Leu
            260                 265                 270

Val Asp Ala Ala Val Asp Ala Gly Leu Trp Ala Arg Asp His Ser Asp
        275                 280                 285

Ala Val Thr Ser Leu His Ala Ala Asn Leu Gly Val Ser Thr Gly Ala
290                 295                 300

Val Gly Gln Gly Phe Gly Ala Asp Phe Gln Gln Arg Leu Val Pro Arg
305                 310                 315                 320

Leu Asp His Asp Ala Leu Ala Leu Leu Glu Arg Thr Gln Gln Phe Leu
                325                 330                 335

Leu Thr Asn Asn Leu Leu Gln Glu Pro Val Ala Leu Asp Gln Trp Ala
            340                 345                 350

Ala Pro Glu Phe Leu Asn Asn Ser Leu Asn Arg His Arg
        355                 360                 365

<210> SEQ ID NO 14
<211> LENGTH: 417
<212> TYPE: PRT
<213> ORGANISM: Rhodococcus
```

<400> SEQUENCE: 14

```
Met Thr Leu Ser Pro Glu Lys Gln His Val Arg Pro Arg Asp Ala Ala
1               5                   10                  15
Asp Asn Asp Pro Val Ala Val Ala Arg Gly Leu Ala Glu Lys Trp Arg
                20                  25                  30
Ala Thr Ala Val Glu Arg Asp Arg Ala Gly Ser Ala Thr Ala Glu
        35                  40                  45
Arg Glu Asp Leu Arg Ala Ser Gly Leu Leu Ser Leu Leu Val Pro Arg
    50                  55                  60
Glu Tyr Gly Gly Trp Gly Ala Asp Trp Pro Thr Ala Ile Glu Val Val
65                  70                  75                  80
Arg Glu Ile Ala Ala Ala Asp Gly Ser Leu Gly His Leu Phe Gly Tyr
                85                  90                  95
His Leu Thr Asn Ala Pro Met Ile Glu Leu Ile Gly Ser Gln Glu Gln
                100                 105                 110
Glu Glu His Leu Tyr Thr Gln Ile Ala Gln Asn Asn Trp Trp Thr Gly
            115                 120                 125
Asn Ala Ser Ser Glu Asn Asn Ser His Val Leu Asp Trp Lys Val Ser
    130                 135                 140
Ala Thr Pro Thr Glu Asp Gly Gly Tyr Val Leu Asn Gly Thr Lys His
145                 150                 155                 160
Phe Cys Ser Gly Ala Lys Gly Ser Asp Leu Leu Phe Val Phe Gly Val
                165                 170                 175
Val Gln Asp Asp Ser Pro Gln Gln Gly Ala Ile Ile Ala Ala Ala Ile
                180                 185                 190
Pro Thr Ser Arg Ala Gly Val Thr Pro Asn Asp Asp Trp Ala Ala Ile
            195                 200                 205
Gly Met Arg Gln Thr Asp Ser Gly Ser Thr Asp Phe His Asn Val Lys
    210                 215                 220
Val Glu Pro Asp Glu Val Leu Gly Ala Pro Asn Ala Phe Val Leu Ala
225                 230                 235                 240
Phe Ile Gln Ser Glu Arg Gly Ser Leu Phe Ala Pro Ile Ala Gln Leu
                245                 250                 255
Ile Phe Ala Asn Val Tyr Leu Gly Ile Ala His Gly Ala Leu Asp Ala
                260                 265                 270
Ala Arg Glu Tyr Thr Arg Thr Gln Ala Arg Pro Trp Thr Pro Ala Gly
            275                 280                 285
Ile Gln Gln Ala Thr Glu Asp Pro Tyr Thr Ile Arg Ser Tyr Gly Glu
    290                 295                 300
Phe Thr Ile Ala Leu Gln Gly Ala Asp Ala Ala Arg Glu Ala Ala
305                 310                 315                 320
His Leu Leu Gln Thr Val Trp Asp Lys Gly Asp Ala Leu Thr Pro Glu
                325                 330                 335
Asp Arg Gly Glu Leu Met Val Lys Val Ser Gly Val Lys Ala Leu Ala
                340                 345                 350
Thr Asn Ala Ala Leu Asn Ile Ser Ser Gly Val Phe Glu Val Ile Gly
            355                 360                 365
Ala Arg Gly Thr His Pro Arg Tyr Gly Phe Asp Arg Phe Trp Arg Asn
    370                 375                 380
Val Arg Thr His Ser Leu His Asp Pro Val Ser Tyr Lys Ile Ala Asp
385                 390                 395                 400
```

```
-continued
Val Gly Lys His Thr Leu Asn Gly Gln Tyr Pro Ile Pro Gly Phe Thr
            405                 410                 415
Ser
```